(12) United States Patent
Kim et al.

(10) Patent No.: US 8,288,357 B2
(45) Date of Patent: Oct. 16, 2012

(54) USE OF INHIBITORS OF LEUKOTRIENE B4 RECEPTOR BLT2 FOR TREATING HUMAN CANCERS

(75) Inventors: Jae-Hong Kim, Goyang-si (KR); Jung-A Choi, Seoul (KR); Eun-Young Kim, Seoul (KR); Geun-Young Kim, Chungju-si (KR); Chul-Min Kim, Masan-si (KR); Ji-Min Seo, Seoul (KR); Hyun-Ju Kim, Incheon (KR); Jin-Wook Lee, Daejeon (KR)

(73) Assignee: Korea University Research & Business Foundation, Seoul (KR)

( * ) Notice: Subject to any disclaimer, the term of this patent is extended or adjusted under 35 U.S.C. 154(b) by 309 days.

(21) Appl. No.: 12/450,335

(22) PCT Filed: Mar. 24, 2008

(86) PCT No.: PCT/KR2008/001649
§ 371 (c)(1),
(2), (4) Date: Sep. 22, 2009

(87) PCT Pub. No.: WO2008/117970
PCT Pub. Date: Oct. 2, 2008

(65) Prior Publication Data
US 2011/0223152 A1      Sep. 15, 2011

Related U.S. Application Data

(60) Provisional application No. 60/896,499, filed on Mar. 23, 2007, provisional application No. 60/896,504, filed on Mar. 23, 2007.

(51) Int. Cl.
*A61K 31/70* (2006.01)
*C07H 21/02* (2006.01)
*C07H 21/04* (2006.01)

(52) U.S. Cl. .............. 514/44 A; 536/24.1; 536/24.5
(58) Field of Classification Search .............. 514/44; 536/24.1, 24.5
See application file for complete search history.

(56) References Cited

FOREIGN PATENT DOCUMENTS
EU          1 745 800  A1      1/2007

OTHER PUBLICATIONS

Chirurgisches Forum 2007 Deutsche Gesellschaft für Chirurgie, 2007, vol. 36, VI., Abstract Only René Hennig, T. Osman, S. Noor, I. Esposito, N. Giese, T. Yokomizo, S. M. Rao, T. E. Adrian and H. Friess.*

(Continued)

*Primary Examiner* — Terra Cotta Gibbs
(74) *Attorney, Agent, or Firm* — Edwards Wildman Palmer LLP; Kongsik Kim, Esq.; Elbert Chiang

(57) ABSTRACT

The present invention relates to a new use of inhibitors of leukotriene B4 receptor BLT2 for treating human cancers. More particularly, the present invention relates to a pharmaceutical composition for treating human cancers comprising BLT2 inhibitors and a method for treating human cancers using BLT2 inhibitors.

The present inventors revealed the role of BLT2 as a survival factor of human cancers, such as bladder, prostate, pancreatic, and breast cancer and found that the BLT2 inhibitors can be used as anti-cancer drugs. The present inventors revealed that BLT2 has an important role in metastasis of cancer cells and angiogenesis of tumor and demonstrated that the anti-cancer activity of the BLT2 inhibitors is accomplished by inducing the apoptosis of cancer cells, inhibiting the metastasis of cancer cells, or inhibiting the angiogenesis of tumor.

14 Claims, 12 Drawing Sheets

OTHER PUBLICATIONS

Choi et al. (Free Radical Biology & Medicine 44 (2008) pp. 624-634, Available online Oct. 26, 2007.*

Biroccio et al. (Oncogene, 2003 vol. 22:6579-6588).*

Ding, XZ, et al., "A novel anti-pancreatic cancer agent, LY293111," Anticancer Drugs, vol. 16, No. 5, pp. 467-473 (Jun. 2005).

Tong, Wei-Gang, et al., "Leukotriene B4 Receptor Antagonist LY293111 Inhibits Proliferation and Induces Apoptosis in Human Pancreatic Cancer Cells," Clin. Cancer Res., vol. 3232, No. 8, pp. 3232-3242 (2002).

Yokomizo, T. et al., "Hydroxyeicosanoids Bind to and Activate the Low Affinity Leukotriene B4 Receptor, BLT2," the Jrl. of Biol. Chem., vol. 276, No. 15, pp. 12454-12459 (Apr. 13, 2001).

Yoo, Min-Hyuk et al., "Role of the BLT2, a leukotriene B4 receptor, in Ras transformation," Oncogene, vol. 23, pp. 9259-9268 (Oct. 18, 2004).

* cited by examiner

Hoechst 33258 staining at 36 hr after LY255283 treatment

DNA fragmentation assay and cell cycle analysis at 48 hr after LY255283 treatment DNA fragmentation assay at 48 hr after LY255283

MTT assay after 48 hr incubation in the presence of LY255283 or DMSO (MDA-MB-468 breast cancer cell)

| cytoplasmic (Total) | Low | Med | High |
|---|---|---|---|
| Stage 0 (4) | 4 (1) | 0 (1) | 0 (2) |
| Stage 1 (13) | 2 (4) | 5 (5) | 6 (5) |
| Stage 2 (39) | 8 (11) | 13(14) | 18(15) |
| Stage 3 (18) | 6(5) | 18(6) | 4 (7) |

( ) : Expected value

Hepatocellular carcinoma (Liver)

Glioblastoma multiforme (Brain)

Infiltrating ductal carcinoma (Breast)

Invasive squamous cell carcinoma (Skin)

Papillary carcinoma (Thyroid)

Normal  Cancer

SEQUENCE LISTING

```
<160> NUMBER OF SEQ ID NOS: 20

<210> SEQ ID NO 1
<211> LENGTH: 2798
<212> TYPE: DNA
<213> ORGANISM: homo sapiens

<400> SEQUENCE: 1
aaactggccc tggccctgaa ccaaatacct tgaaccctcg taaactccat accctgaccc      60
ccttgttttg gatataccca ggtagaacaa ctctctctca ctgtctgttg tgaggatacg     120
ctgtagccca ctcattaagt acattctcct aataaatgct ttggactgat caccctgcca     180
gtcttttgtc ttgggcaatc tatactttc tcagaggttc ccaaggccta ctgaagggac     240
ttaacatact cttaatggct ttcctctctc ttgttttacc ttatgccctc acttcctgag     300
ttaacctccc aaatacagga tcacctgtac ccaagccctt agctcaagaa tacaggatca     360
cctgtaccca agcccttagc tcaagctctg ctttggaaga acccaaacta agacagtgct     420
```

```
cctggtgccc tccccaagca acctcaagtt ctggctgtta cttgagcaga ggcctttctt    480
ttcccttccc ccagctctat ccatctgcca ggccccctc aaatctcttc atttccaagt    540
tttgcttgac ttttccaaga ggagagggct gcttcttagt atgtccctac tcatcctttc    600
ctttcttgtc ttgtatcctg gtgcagcctg gtaatgggc ctcttcatgg ttgtgtgtca    660
tgactcccta accattatgc ctccatgcat ccctgttcc tcctggaacc tagcaccatg    720
ccttacatgg aaaagctgtc attgacagcc cggtgagagc cctgagggtg gagtgactgg    780
ggcagggcct gaggcaagag gtgggaggag gtaggaggcc aggggctcag ccggaccagg    840
agactggaaa caggcaagga taaggcaggt ggggactga gttgtttggg tcacctctgc    900
aggccagaga gaccaggcaa catacacact gcagaaggtg ggctggagg attggggcca    960 gagctggggg agggatgaga acagaagcag gaccaggatt cagcagagtc ctcctatttc   1020
cttccaccac cagggaatct tactgcccca cttcagcttg tgctgtttcc tggcaaggca   1080
ggctctcaca tgcctggacg cctgggtgcg ttggtgatgg gaaggagcag ggtgagggag   1140 gggcccagg agaggcccag gatgagcctc atcttgtccc tccccattct tgtcttaccc   1200
tctgcaaatg tgataggcac aggacaggag taggcacctc gcctactgct gcttaacctt   1260
tcagcttctc caggccccca atcctgcttg ctcccagctt ggtaagtaga tctgtgcacg   1320 tcccttaca ccccaccatc cagttttgcc cagatgtgct agaatggggc tggacaaaga   1380
aggaggggcc agactagagg agtggtggta gagatagtga cagcctgggg tgaggacttt   1440
atgcctgttt accactgagc tctgggaagg aggccaggag tggggcaggt caactgactg   1500
ggagcagggg atctgggttc caagaaggag ttgtgtttga ggtgggtct gggtcctcgt   1560 ggaagtcagg actcccaggc agaaaagagg caggctgcag ggaagtaagg aggaggcatg   1620
gcaccttctc atcgggcatc acaggtgggg ttttgcccca cccctgaacg ccctctgtgg   1680
cgccttccac ccacctgtag gcccagaagg atgtcggtct gctaccgtcc cccagggaac   1740
gagacactgc tgagctggaa gacttcgcgg gccacaggca cagccttcct gctgctggcg   1800
gcgctgctgg ggctgcctgg caacggcttc gtggtgtgga gcttggcggg ctggcggcct   1860 gcacggggc gaccgctggc ggccacgctt gtgctgcacc tggcgctggc cgacggcgcg   1920
gtgctgctgc tcacgccgct ctttgtggcc ttcctgaccc ggcaggcctg ccgctgggc   1980 caggcgggct gcaaggcggt gtactacgtg tgcgcgctca gcatgtacgc cagcgtgctg   2040
ctcaccggcc tgctcagcct gcagcgctgc ctcgcagtca cccgccccttc ctggcgcct   2100 cggctgcgca gccggccct ggccgccgc ctgctgctgg cggtctggct ggccgccctg   2160
ttgctcgccg tcccggccgc cgtctaccgc cacctgtgga gggaccgcgt atgccagctg   2220 tgccaccgt cgccggtcca cgccgccgcc cacctgagcc tggagactct gaccgctttc   2280
gtgcttcctt tcgggctgat gctcggctgc tacagcgtga cgctggcacg gctgcggggc   2340
gcccgctggg gctccgggcg gcacggggcg cgggtgggcc ggctggtgag cgccatcgtg   2400
cttgccttcg gcttgctctg gcccccctac cacgcagtca accttctgca ggcggtcgca   2460
gcgctggctc caccggaagg ggccttggcg aagctgggcg gagccggcca ggcggcgcga   2520
gcgggaacta cggccttggc cttcttcagt tctagcgtca accggtgct ctacgtcttc   2580 accgctggag atctgctgcc ccgggcaggt ccccgtttcc tcacgcggct cttcgaaggc   2640
tctggggagg cccgaggggg cggccgctct agggaaggga ccatggagct ccgaactacc   2700
cctcagctga aagtggtggg gcaggccgc ggcaatggag accgggggg tgggatggag   2760 aaggacggtc cggaatggga cctttgacag cagaccct                           2798
```

<210> SEQ ID NO 2
<211> LENGTH: 1170
<212> TYPE: DNA
<213> ORGANISM: homo sapiens
<220> FEATURE:
<221> NAME/KEY: CDS
<222> LOCATION: (1)..(1167)

<400> SEQUENCE: 2

| | | | | | | | | | | | | | | | | |
|---|---|---|---|---|---|---|---|---|---|---|---|---|---|---|---|---|
| atg | gca | cct | tct | cat | cgg | gca | tca | cag | gtg | ggg | ttt | tgc | ccc | acc | cct | 48 |
| Met | Ala | Pro | Ser | His | Arg | Ala | Ser | Gln | Val | Gly | Phe | Cys | Pro | Thr | Pro | |
| 1 | | | | 5 | | | | | 10 | | | | | 15 | | |
| gaa | cgc | cct | ctg | tgg | cgc | ctt | cca | ccc | acc | tgt | agg | ccc | aga | agg | atg | 96 |
| Glu | Arg | Pro | Leu | Trp | Arg | Leu | Pro | Pro | Thr | Cys | Arg | Pro | Arg | Arg | Met | |
| | | | 20 | | | | | 25 | | | | | 30 | | | |
| tcg | gtc | tgc | tac | cgt | ccc | cca | ggg | aac | gag | aca | ctg | ctg | agc | tgg | aag | 144 |
| Ser | Val | Cys | Tyr | Arg | Pro | Pro | Gly | Asn | Glu | Thr | Leu | Leu | Ser | Trp | Lys | |
| | | 35 | | | | | 40 | | | | | 45 | | | | |
| act | tcg | cgg | gcc | aca | ggc | aca | gcc | ttc | ctg | ctg | ctg | gcg | gcg | ctg | ctg | 192 |
| Thr | Ser | Arg | Ala | Thr | Gly | Thr | Ala | Phe | Leu | Leu | Leu | Ala | Ala | Leu | Leu | |
| | 50 | | | | | 55 | | | | | 60 | | | | | |
| ggg | ctg | cct | ggc | aac | ggc | ttc | gtg | gtg | tgg | agc | ttg | gcg | ggc | tgg | cgg | 240 |
| Gly | Leu | Pro | Gly | Asn | Gly | Phe | Val | Val | Trp | Ser | Leu | Ala | Gly | Trp | Arg | |
| 65 | | | | | 70 | | | | | 75 | | | | | 80 | |
| cct | gca | cgg | ggg | cga | ccg | ctg | gcg | gcc | acg | ctt | gtg | ctg | cac | ctg | gcg | 288 |
| Pro | Ala | Arg | Gly | Arg | Pro | Leu | Ala | Ala | Thr | Leu | Val | Leu | His | Leu | Ala | |
| | | | | 85 | | | | | 90 | | | | | 95 | | |
| ctg | gcc | gac | ggc | gcg | gtg | ctg | ctg | ctc | acg | ccg | ctc | ttt | gtg | gcc | ttc | 336 |
| Leu | Ala | Asp | Gly | Ala | Val | Leu | Leu | Leu | Thr | Pro | Leu | Phe | Val | Ala | Phe | |
| | | | 100 | | | | | 105 | | | | | 110 | | | |
| ctg | acc | cgg | cag | gcc | tgg | ccg | ctg | ggc | cag | gcg | ggc | tgc | aag | gcg | gtg | 384 |
| Leu | Thr | Arg | Gln | Ala | Trp | Pro | Leu | Gly | Gln | Ala | Gly | Cys | Lys | Ala | Val | |
| | | 115 | | | | | 120 | | | | | 125 | | | | |
| tac | tac | gtg | tgc | gcg | ctc | agc | atg | tac | gcc | agc | gtg | ctg | ctc | acc | ggc | 432 |
| Tyr | Tyr | Val | Cys | Ala | Leu | Ser | Met | Tyr | Ala | Ser | Val | Leu | Leu | Thr | Gly | |
| | 130 | | | | | 135 | | | | | 140 | | | | | |
| ctg | ctc | agc | ctg | cag | cgc | tgc | ctc | gca | gtc | acc | cgc | ccc | ttc | ctg | gcg | 480 |
| Leu | Leu | Ser | Leu | Gln | Arg | Cys | Leu | Ala | Val | Thr | Arg | Pro | Phe | Leu | Ala | |
| 145 | | | | | 150 | | | | | 155 | | | | | 160 | |
| cct | cgg | ctg | cgc | agc | ccg | gcc | ctg | gcc | cgc | cgc | ctg | ctg | gcg | gtc | | 528 |
| Pro | Arg | Leu | Arg | Ser | Pro | Ala | Leu | Ala | Arg | Arg | Leu | Leu | Ala | Val | | |
| | | | | 165 | | | | | 170 | | | | | 175 | | |
| tgg | ctg | gcc | gcc | ctg | ttg | ctc | gcc | gtc | ccg | gcc | gcc | gtc | tac | cgc | cac | 576 |
| Trp | Leu | Ala | Ala | Leu | Leu | Leu | Ala | Val | Pro | Ala | Ala | Val | Tyr | Arg | His | |
| | | | 180 | | | | | 185 | | | | | 190 | | | |
| ctg | tgg | agg | gac | cgc | gta | tgc | cag | ctg | tgc | cac | ccg | tcg | ccg | gtc | cac | 624 |
| Leu | Trp | Arg | Asp | Arg | Val | Cys | Gln | Leu | Cys | His | Pro | Ser | Pro | Val | His | |
| | | 195 | | | | | 200 | | | | | 205 | | | | |
| gcc | gcc | gcc | cac | ctg | agc | ctg | gag | act | ctg | acc | gct | ttc | gtg | ctt | cct | 672 |
| Ala | Ala | Ala | His | Leu | Ser | Leu | Glu | Thr | Leu | Thr | Ala | Phe | Val | Leu | Pro | |
| | 210 | | | | | 215 | | | | | 220 | | | | | |
| ttc | ggg | ctg | atg | ctc | ggc | tgc | tac | agc | gtg | acg | ctg | gca | cgg | ctg | cgg | 720 |
| Phe | Gly | Leu | Met | Leu | Gly | Cys | Tyr | Ser | Val | Thr | Leu | Ala | Arg | Leu | Arg | |
| 225 | | | | | 230 | | | | | 235 | | | | | 240 | |
| ggc | gcc | cgc | tgg | ggc | tcc | ggg | cgg | cac | ggg | gcg | cgg | gtg | ggc | cgg | ctg | 768 |
| Gly | Ala | Arg | Trp | Gly | Ser | Gly | Arg | His | Gly | Ala | Arg | Val | Gly | Arg | Leu | |
| | | | | 245 | | | | | 250 | | | | | 255 | | |
| gtg | agc | gcc | atc | gtg | ctt | gcc | ttc | ggc | ttg | ctc | tgg | gcc | ccc | tac | cac | 816 |
| Val | Ser | Ala | Ile | Val | Leu | Ala | Phe | Gly | Leu | Leu | Trp | Ala | Pro | Tyr | His | |
| | | | 260 | | | | | 265 | | | | | 270 | | | |
| gca | gtc | aac | ctt | ctg | cag | gcg | gtc | gca | gcg | ctg | gct | cca | ccg | gaa | ggg | 864 |

```
Ala Val Asn Leu Leu Gln Ala Val Ala Ala Leu Ala Pro Pro Glu Gly
        275                 280                 285 gcc ttg gcg aag ctg ggc gga gcc ggc cag gcg gcg cga gcg gga act    912
Ala Leu Ala Lys Leu Gly Gly Ala Gly Gln Ala Ala Arg Ala Gly Thr
        290                 295                 300 acg gcc ttg gcc ttc ttc agt tct agc gtc aac ccg gtg ctc tac gtc    960
Thr Ala Leu Ala Phe Phe Ser Ser Ser Val Asn Pro Val Leu Tyr Val
305                 310                 315                 320 ttc acc gct gga gat ctg ctg ccc cgg gca ggt ccc cgt ttc ctc acg   1008
Phe Thr Ala Gly Asp Leu Leu Pro Arg Ala Gly Pro Arg Phe Leu Thr
                325                 330                 335 cgg ctc ttc gaa ggc tct ggg gag gcc cga ggg ggc ggc cgc tct agg   1056
Arg Leu Phe Glu Gly Ser Gly Glu Ala Arg Gly Gly Gly Arg Ser Arg
                340                 345                 350 gaa ggg acc atg gag ctc cga act acc cct cag ctg aaa gtg gtg ggg   1104
Glu Gly Thr Met Glu Leu Arg Thr Thr Pro Gln Leu Lys Val Val Gly
            355                 360                 365 cag ggc cgc ggc aat gga gac ccg ggg ggt ggg atg gag aag gac ggt   1152
Gln Gly Arg Gly Asn Gly Asp Pro Gly Gly Gly Met Glu Lys Asp Gly
370                 375                 380 ccg gaa tgg gac ctt tga                                            1170
Pro Glu Trp Asp Leu
385
```

<210> SEQ ID NO 3
<211> LENGTH: 389
<212> TYPE: PRT
<213> ORGANISM: homo sapiens

<400> SEQUENCE: 3

```
Met Ala Pro Ser His Arg Ala Ser Gln Val Gly Phe Cys Pro Thr Pro
  1               5                  10                  15

Glu Arg Pro Leu Trp Arg Leu Pro Pro Thr Cys Arg Pro Arg Arg Met
             20                  25                  30

Ser Val Cys Tyr Arg Pro Pro Gly Asn Glu Thr Leu Leu Ser Trp Lys
         35                  40                  45

Thr Ser Arg Ala Thr Gly Thr Ala Phe Leu Leu Ala Ala Leu Leu
     50                  55                  60

Gly Leu Pro Gly Asn Gly Phe Val Val Trp Ser Leu Ala Gly Trp Arg
 65                  70                  75                  80

Pro Ala Arg Gly Arg Pro Leu Ala Ala Thr Leu Val Leu His Leu Ala
                 85                  90                  95

Leu Ala Asp Gly Ala Val Leu Leu Thr Pro Leu Phe Val Ala Phe
            100                 105                 110

Leu Thr Arg Gln Ala Trp Pro Leu Gly Gln Ala Gly Cys Lys Ala Val
        115                 120                 125

Tyr Tyr Val Cys Ala Leu Ser Met Tyr Ala Ser Val Leu Leu Thr Gly
    130                 135                 140

Leu Leu Ser Leu Gln Arg Cys Leu Ala Val Thr Arg Pro Phe Leu Ala
145                 150                 155                 160

Pro Arg Leu Arg Ser Pro Ala Leu Ala Arg Arg Leu Leu Ala Val
                165                 170                 175

Trp Leu Ala Ala Leu Leu Leu Ala Val Pro Ala Ala Val Tyr Arg His
            180                 185                 190

Leu Trp Arg Asp Arg Val Cys Gln Leu Cys His Pro Ser Pro Val His
        195                 200                 205

Ala Ala Ala His Leu Ser Leu Glu Thr Leu Thr Ala Phe Val Leu Pro
    210                 215                 220
```

```
Phe Gly Leu Met Leu Gly Cys Tyr Ser Val Thr Leu Ala Arg Leu Arg
225                 230                 235                 240

Gly Ala Arg Trp Gly Ser Gly Arg His Gly Ala Arg Val Gly Arg Leu
            245                 250                 255

Val Ser Ala Ile Val Leu Ala Phe Gly Leu Leu Trp Ala Pro Tyr His
                260                 265                 270

Ala Val Asn Leu Leu Gln Ala Val Ala Ala Leu Ala Pro Pro Glu Gly
            275                 280                 285

Ala Leu Ala Lys Leu Gly Gly Ala Gly Gln Ala Arg Ala Gly Thr
        290                 295                 300

Thr Ala Leu Ala Phe Phe Ser Ser Ser Val Asn Pro Val Leu Tyr Val
305                 310                 315                 320

Phe Thr Ala Gly Asp Leu Leu Pro Arg Ala Gly Pro Arg Phe Leu Thr
                325                 330                 335

Arg Leu Phe Glu Gly Ser Gly Glu Ala Arg Gly Gly Arg Ser Arg
            340                 345                 350

Glu Gly Thr Met Glu Leu Arg Thr Thr Pro Gln Leu Lys Val Val Gly
        355                 360                 365

Gln Gly Arg Gly Asn Gly Asp Pro Gly Gly Met Glu Lys Asp Gly
    370                 375                 380

Pro Glu Trp Asp Leu
385

<210> SEQ ID NO 4
<211> LENGTH: 1077
<212> TYPE: DNA
<213> ORGANISM: homo sapiens
<220> FEATURE:
<221> NAME/KEY: CDS
<222> LOCATION: (1)..(1074)

<400> SEQUENCE: 4 atg tcg gtc tgc tac cgt ccc cca ggg aac gag aca ctg ctg agc tgg        48
Met Ser Val Cys Tyr Arg Pro Pro Gly Asn Glu Thr Leu Leu Ser Trp
1               5                   10                  15 aag act tcg cgg gcc aca ggc aca gcc ttc ctg ctg ctg gcg gcg ctg        96
Lys Thr Ser Arg Ala Thr Gly Thr Ala Phe Leu Leu Leu Ala Ala Leu
            20                  25                  30 ctg ggg ctg cct ggc aac ggc ttc gtg gtg tgg agc ttg gcg ggc tgg       144
Leu Gly Leu Pro Gly Asn Gly Phe Val Val Trp Ser Leu Ala Gly Trp
        35                  40                  45 cgg cct gca cgg ggg cga ccg ctg gcg gcc acg ctt gtg ctg cac ctg       192
Arg Pro Ala Arg Gly Arg Pro Leu Ala Ala Thr Leu Val Leu His Leu
    50                  55                  60 gcg ctg gcc gac ggc gcg gtg ctg ctc acg ccg ctc ttt gtg gcc           240
Ala Leu Ala Asp Gly Ala Val Leu Leu Leu Thr Pro Leu Phe Val Ala
65                  70                  75                  80 ttc ctg acc cgg cag gcc tgg ccg ctg ggc cag gcg ggc tgc aag gcg       288
Phe Leu Thr Arg Gln Ala Trp Pro Leu Gly Gln Ala Gly Cys Lys Ala
                85                  90                  95 gtg tac tac gtg tgc gcg ctc agc atg tac gcc agc gtg ctg ctc acc       336
Val Tyr Tyr Val Cys Ala Leu Ser Met Tyr Ala Ser Val Leu Leu Thr
            100                 105                 110 ggc ctg ctc agc ctg cag cgc tgc ctc gca gtc acc cgc ccc ttc ctg       384
Gly Leu Leu Ser Leu Gln Arg Cys Leu Ala Val Thr Arg Pro Phe Leu
        115                 120                 125 gcg cct cgg ctg cgc agc ccg gcc ctg gcc cgc cgc ctg ctg ctg gcg       432
Ala Pro Arg Leu Arg Ser Pro Ala Leu Ala Arg Arg Leu Leu Leu Ala
    130                 135                 140
```

```
gtc tgg ctg gcc gcc ctg ttg ctc gcc gtc ccg gcc gcc gtc tac cgc     480
Val Trp Leu Ala Ala Leu Leu Leu Ala Val Pro Ala Ala Val Tyr Arg
145                 150                 155                 160 cac ctg tgg agg gac cgc gta tgc cag ctg tgc cac ccg tcg ccg gtc     528
His Leu Trp Arg Asp Arg Val Cys Gln Leu Cys His Pro Ser Pro Val
                165                 170                 175 cac gcc gcc gcc cac ctg agc ctg gag act ctg acc gct ttc gtg ctt     576
His Ala Ala Ala His Leu Ser Leu Glu Thr Leu Thr Ala Phe Val Leu
            180                 185                 190 cct ttc ggg ctg atg ctc ggc tgc tac agc gtg acg ctg gca cgg ctg     624
Pro Phe Gly Leu Met Leu Gly Cys Tyr Ser Val Thr Leu Ala Arg Leu
        195                 200                 205 cgg ggc gcc cgc tgg ggc tcc ggg cgg cac ggg gcg cgg gtg ggc cgg     672
Arg Gly Ala Arg Trp Gly Ser Gly Arg His Gly Ala Arg Val Gly Arg
    210                 215                 220 ctg gtg agc gcc atc gtg ctt gcc ttc ggc ttg ctc tgg gcc ccc tac     720
Leu Val Ser Ala Ile Val Leu Ala Phe Gly Leu Leu Trp Ala Pro Tyr
225                 230                 235                 240 cac gca gtc aac ctt ctg cag gcg gtc gca gcg ctg gct cca ccg gaa     768
His Ala Val Asn Leu Leu Gln Ala Val Ala Ala Leu Ala Pro Pro Glu
                245                 250                 255 ggg gcc ttg gcg aag ctg gga gcc ggc cag gcg gcg cga gcg gga     816
Gly Ala Leu Ala Lys Leu Gly Gly Ala Gly Gln Ala Ala Arg Ala Gly
            260                 265                 270 act acg gcc ttg gcc ttc ttc agt tct agc gtc aac ccg gtg ctc tac     864
Thr Thr Ala Leu Ala Phe Phe Ser Ser Ser Val Asn Pro Val Leu Tyr
        275                 280                 285 gtc ttc acc gct gga gat ctg ctg ccc cgg gca ggt ccc cgt ttc ctc     912
Val Phe Thr Ala Gly Asp Leu Leu Pro Arg Ala Gly Pro Arg Phe Leu
    290                 295                 300 acg cgg ctc ttc gaa ggc tct ggg gag gcc cga ggg ggc ggc cgc tct     960
Thr Arg Leu Phe Glu Gly Ser Gly Glu Ala Arg Gly Gly Gly Arg Ser
305                 310                 315                 320 agg gaa ggg acc atg gag ctc cga act acc cct cag ctg aaa gtg gtg    1008
Arg Glu Gly Thr Met Glu Leu Arg Thr Thr Pro Gln Leu Lys Val Val
                325                 330                 335 ggg cag ggc cgc ggc aat gga gac ccg ggg ggt ggg atg gag aag gac    1056
Gly Gln Gly Arg Gly Asn Gly Asp Pro Gly Gly Gly Met Glu Lys Asp
            340                 345                 350 ggt ccg gaa tgg gac ctt tga                                        1077
Gly Pro Glu Trp Asp Leu
        355

<210> SEQ ID NO 5
<211> LENGTH: 358
<212> TYPE: PRT
<213> ORGANISM: homo sapiens

<400> SEQUENCE: 5

Met Ser Val Cys Tyr Arg Pro Pro Gly Asn Glu Thr Leu Leu Ser Trp
1               5                   10                  15

Lys Thr Ser Arg Ala Thr Gly Thr Ala Phe Leu Leu Leu Ala Ala Leu
            20                  25                  30

Leu Gly Leu Pro Gly Asn Gly Phe Val Val Trp Ser Leu Ala Gly Trp
        35                  40                  45

Arg Pro Ala Arg Gly Arg Pro Leu Ala Ala Thr Leu Val Leu His Leu
    50                  55                  60

Ala Leu Ala Asp Gly Ala Val Leu Leu Leu Thr Pro Leu Phe Val Ala
65                  70                  75                  80
```

```
Phe Leu Thr Arg Gln Ala Trp Pro Leu Gly Gln Ala Gly Cys Lys Ala
             85                  90                  95
Val Tyr Tyr Val Cys Ala Leu Ser Met Tyr Ala Ser Val Leu Leu Thr
            100                 105                 110
Gly Leu Leu Ser Leu Gln Arg Cys Leu Ala Val Thr Arg Pro Phe Leu
            115                 120                 125
Ala Pro Arg Leu Arg Ser Pro Ala Leu Ala Arg Arg Leu Leu Leu Ala
        130                 135                 140
Val Trp Leu Ala Ala Leu Leu Ala Val Pro Ala Ala Val Tyr Arg
145                 150                 155                 160
His Leu Trp Arg Asp Arg Val Cys Gln Leu Cys His Pro Ser Pro Val
                165                 170                 175
His Ala Ala Ala His Leu Ser Leu Glu Thr Leu Thr Ala Phe Val Leu
            180                 185                 190
Pro Phe Gly Leu Met Leu Gly Cys Tyr Ser Val Thr Leu Ala Arg Leu
            195                 200                 205
Arg Gly Ala Arg Trp Gly Ser Gly Arg His Gly Ala Arg Val Gly Arg
        210                 215                 220
Leu Val Ser Ala Ile Val Leu Ala Phe Gly Leu Leu Trp Ala Pro Tyr
225                 230                 235                 240
His Ala Val Asn Leu Leu Gln Ala Val Ala Ala Leu Ala Pro Pro Glu
                245                 250                 255
Gly Ala Leu Ala Lys Leu Gly Gly Ala Gly Gln Ala Ala Arg Ala Gly
            260                 265                 270
Thr Thr Ala Leu Ala Phe Phe Ser Ser Val Asn Pro Val Leu Tyr
        275                 280                 285
Val Phe Thr Ala Gly Asp Leu Leu Pro Arg Ala Gly Pro Arg Phe Leu
290                 295                 300
Thr Arg Leu Phe Glu Gly Ser Gly Glu Ala Arg Gly Gly Arg Ser
305                 310                 315                 320
Arg Glu Gly Thr Met Glu Leu Arg Thr Thr Pro Gln Leu Lys Val Val
                325                 330                 335
Gly Gln Gly Arg Gly Asn Gly Asp Pro Gly Gly Met Glu Lys Asp
            340                 345                 350
Gly Pro Glu Trp Asp Leu
        355

<210> SEQ ID NO 6
<211> LENGTH: 15
<212> TYPE: DNA
<213> ORGANISM: Artificial Sequence
<220> FEATURE:
<223> OTHER INFORMATION: hBLT2 anti-sense sequence

<400> SEQUENCE: 6
cagcagtgtc tcgtt                                                    15

<210> SEQ ID NO 7
<211> LENGTH: 21
<212> TYPE: RNA
<213> ORGANISM: Artificial Sequence
<220> FEATURE:
<223> OTHER INFORMATION: hBLT2 siRNA sense sequence

<400> SEQUENCE: 7
gaaggauguc ggucugcuau u                                             21

<210> SEQ ID NO 8
```

-continued

```
<211> LENGTH: 21
<212> TYPE: RNA
<213> ORGANISM: Artificial Sequence
<220> FEATURE:
<223> OTHER INFORMATION: hBLT2 siRNA antisense sequence

<400> SEQUENCE: 8
uagcagaccg acauccuucu u                                              21

<210> SEQ ID NO 9
<211> LENGTH: 25
<212> TYPE: DNA
<213> ORGANISM: Artificial Sequence
<220> FEATURE:
<223> OTHER INFORMATION: forward primer for hBLT2

<400> SEQUENCE: 9
agcctggaga ctctgaccgc tttcg                                          25

<210> SEQ ID NO 10
<211> LENGTH: 25
<212> TYPE: DNA
<213> ORGANISM: Artificial Sequence
<220> FEATURE:
<223> OTHER INFORMATION: reverse primer for hBLT2

<400> SEQUENCE: 10
gacgtagagc accgggttga cgcta                                          25

<210> SEQ ID NO 11
<211> LENGTH: 20
<212> TYPE: DNA
<213> ORGANISM: Artificial Sequence
<220> FEATURE:
<223> OTHER INFORMATION: forward primer for re-hBLT2

<400> SEQUENCE: 11
tctcatcggg catcacaggt                                                20

<210> SEQ ID NO 12
<211> LENGTH: 20
<212> TYPE: DNA
<213> ORGANISM: Artificial Sequence
<220> FEATURE:
<223> OTHER INFORMATION: reverse primer for re-hBLT2

<400> SEQUENCE: 12
ccaagctcca caccacgaag                                                20

<210> SEQ ID NO 13
<211> LENGTH: 20
<212> TYPE: DNA
<213> ORGANISM: Artificial Sequence
<220> FEATURE:
<223> OTHER INFORMATION: forward primer 1 for BLT2

<400> SEQUENCE: 13
gcgcagggac ttcctttgtc                                                20

<210> SEQ ID NO 14
<211> LENGTH: 21
<212> TYPE: DNA
<213> ORGANISM: Artificial Sequence
<220> FEATURE:
<223> OTHER INFORMATION: forward primer 2 for BLT2

<400> SEQUENCE: 14
```

```
gctctagagc ctctgctaacc                                          21

<210> SEQ ID NO 15
<211> LENGTH: 21
<212> TYPE: DNA
<213> ORGANISM: Artificial Sequence
<220> FEATURE:
<223> OTHER INFORMATION: reverse primer for BLT2

<400> SEQUENCE: 15
ccgatgggtg gcacaattgac                                          21

<210> SEQ ID NO 16
<211> LENGTH: 20
<212> TYPE: DNA
<213> ORGANISM: Artificial Sequence
<220> FEATURE:
<223> OTHER INFORMATION: forward primer for mBLT2

<400> SEQUENCE: 16
cagcatgtac gccagcgtgc                                           20

<210> SEQ ID NO 17
<211> LENGTH: 19
<212> TYPE: DNA
<213> ORGANISM: Artificial Sequence
<220> FEATURE:
<223> OTHER INFORMATION: reverse primer for mBLT2

<400> SEQUENCE: 17
cgatggcgct caccagacc                                            19

<210> SEQ ID NO 18
<211> LENGTH: 19
<212> TYPE: DNA
<213> ORGANISM: Artificial Sequence
<220> FEATURE:
<223> OTHER INFORMATION: BLT2 anti-sense sequence

<400> SEQUENCE: 18
gaaggatgtc ggtctgcta                                            19

<210> SEQ ID NO 19
<211> LENGTH: 20
<212> TYPE: DNA
<213> ORGANISM: Artificial Sequence
<220> FEATURE:
<223> OTHER INFORMATION: forward primer for BLT2 coding region

<400> SEQUENCE: 19
cttctcatcg ggcatcacag                                           20

<210> SEQ ID NO 20
<211> LENGTH: 20
<212> TYPE: DNA
<213> ORGANISM: Artificial Sequence
<220> FEATURE:
<223> OTHER INFORMATION: reverse primer for BLT2 coding region

<400> SEQUENCE: 20
atccttctgg gcctacaggt                                           20
```

USE OF INHIBITORS OF LEUKOTRIENE B4 RECEPTOR BLT2 FOR TREATING HUMAN CANCERS

This is a National Phase Application filed under 35 USC 371 of International Application No. PCT/KR2008/001649, filed on Mar. 24, 2008, an application claiming the benefit under 35 USC 119(e) of U.S. Provisional Application No. 60/896,499, filed on Mar. 23, 2007, and claiming the benefit under 35 USC 119(e) of U.S. Provisional Application No. 60/896,504, filed on Mar. 23, 2007.

TECHNICAL FIELD

The present invention relates to a new use of inhibitors of leukotriene B4 receptor BLT2 for treating human cancers. More particularly, the present invention relates to a pharmaceutical composition for treating human cancers comprising BLT2 inhibitors and a method for treating human cancers using BLT2 inhibitors.

BACKGROUND ART

Leukotrienes are a family of inflammatory lipid mediators that are derived from arachidonic acid (AA) by the action of 5-lipoxygenase (5-LO) and 5-lipoxygenase activating protein (FLAP), which mediate acute and chronic inflammation. Leukotriene $B_4$ ($LTB_4$), the first leukotriene isolated, elicits a variety of inflammatory responses, including leukocyte activation, chemotaxis and degranulation (Samuelsson, 1987; Woo, 2002; Yokimizo, 1997). In addition, overproduction of $LTB_4$ is involved in such inflammation-related ailments as bronchial asthma and rheumatoid arthritis (Chen, 1994; Griffiths, 1995; Turner, 1996). It is known that $LTB_4$ produces its biological effects by binding to its receptors, BLT1 and BLT2 (Yokimizo, 1997; Choi, 2008). Most studies of $LTB_4$ receptors have focused on the high-affinity receptor, BLT1, which is expressed exclusively in inflammatory cells such as leukocytes, and plays a role in inflammatory processes (Yokimizo, 1997). In contrast to BLT1, BLT2 has a low affinity for $LTB_4$ and is expressed in a wide variety of tissues, with highest levels in spleen, leukocytes and ovary (Yokimizo, 1997; Kamohara, 2000). No clear physiological function has yet been identified for BLT2. Recently, BLT2 has been recognized as a downstream component of oncogenic Ras, thereby mediating Ras transformation (Choi, 2008). Consistent with the proposed role of 'ptg$LTB_4$-BLT2'-cascade as downstream component of Ras signaling, enhanced production of $LTB_4$ has been noted in Rat2-HO6 cells (Yoo, 2004). Interestingly, we also observed some enhanced production of $LTB_4$ in Rat2-BLT2 cells overexpressing BLT2 (Yoo, 2004), suggesting the possibility of crosstalk between $LTB_4$ and BLT2 such that each triggers induction of the other. These findings suggest that the transformed phenotype are elicited by an autocrine or paracrine effect of the high level of $LTB_4$ acting via BLT2 to amplify the $LTB_4$-dependent cascade. In agreement with the proposed function of $LTB_4$ and BLT2 as downstream intermediates in H-Ras$^{V12}$ signaling, Rat2-HO6 cells which express oncogenic H-Ras$^{V12}$ cells had increased levels of $cPLA_2$, 5-LO and FLAP, three proteins involved in the synthesis of $LTB_4$ (Yoo, 2004). In that regard, $cPLA_2$ expression is also upregulated in a number of cancer cell lines, and contributes to induction of the transformed phenotypes (Blaine, 2001; Heasley, 1997). Similarly, 5-LO is upregulated in human pancreatic, breast and prostate cancers (Gupta, 2001; Hennig, 2002; Jiang, 2003; Matsuyama, 2004). In addition, 5-LO and $LTB_4$ receptors are highly expressed in human pancreatic cancers, but not in normal pancreatic duct tissue (Jiang, 2003; Ding, 2005), and the $LTB_4$ receptor BLT1 antagonist LY293111 inhibits the growth and induces apoptosis of human pancreatic cancer cells (Tong, 2002). However, the role of BLT2 in malignant transformation remains to be elucidated.

Based on above background, this invention is to make use of BLT2 inhibitors for (1) inducing apoptosis of cancer cells, (2) suppressing metastatic potential of cancer cells, (3) blocking angiogenesis of cancer cells. Also, this invention include (4) a novel strategy for screeing BLT2 signaling inhibitors by measuring the cell growth of Rat2-BLT2 stable cells. Lastly, this invention includes (5) the novel observation of BLT2 overexpression in various human cancers, which is a critical phenomena in tumorigenesis. Thus, this invention claims any use of strategy targeting against BLT2 overexpression or over-activation as a tool for developing therapeutic composition against human cancer.

Throughout this application, several patents and publications are referenced or cited in parentheses. The disclosure of these patents and publications is incorporated into this application in order to more fully describe this invention and the state of the art to which this invention pertains.

DISCLOSURE OF INVENTION

The object of the present invention is to provide a new use of BLT2 inhibitors for the manufacture of a medicament for the treatment of human cancer.

Further, another object of the present invention is to provide a pharmaceutical composition for the treatment of human cancer comprising BLT2 inhibitors as an active ingredient.

Further, another object of the present invention is to provide a method for treating a patient with cancer, which comprises administering of BLT2 inhibitors to the patient.

Further, another object of the present invention is to provide a method for screening a substance for treating human cancer, which comprises determining whether to reduce the expression or signaling level of BLT2.

Further, another object of the present invention is to provide a kit for detecting human cancer, which comprises a primer or probe for detecting BLT2 gene or an antibody from detecting BLT2 protein.

Other objects and advantage of the present invention will become apparent from the detailed description to follow taken in conjugation with the appended claims and drawings.

This invention is based on the finding that BLT2 inhibition leads to enhanced apoptosis in human cancer cells and also to suppressed metastasis of human cancer cells. Additionally, the combined use of BLT2 antagonist LY255283 with epirubicin or other chemotherapeutic agents causes a synergistic apoptosis of human breast cancer cells. By employing a novel BLT2 inhibitors such as BLT2 siRNA or antisense oligonucleotide, many BLT2-signaling inhibitory effect were observed. Thus, this invention is about a novel composition containing LY255283, BLT2 antisense oligonucleotide, or other BLT2 signaling inhibitors for preparing therapeutic agents against various human cancers such as bladder cancer, breast cancer, prostate cancer, and pancreatic cancer. This invention is also based on the finding that in most human cancers including bladder cancer, breast cancer, prostate cancer, pancreatic cancer, brain cancer, skin cancer, and liver cancer, BLT2 is highly overexpressed compared to normal tissues which express a minimal amount of BLT2. And this invention is based on the finding that the overexpressed BLT2 and its over-activated signaling play critical roles in mediating the tumorigenesis. Thus, this invention includes any use of strategy targeting BLT2 overexpression or over-activation as a way for developing therapeutic composition against human cancer.

According to one aspect of the present invention, there is provided a use of a substance that inhibits the expression or intracellular signaling of BLT2 for the manufacture of a medicament for the treatment of human cancer. In this specification, the phrase "inhibit(s) the expression of BLT2" means to inhibit any step among the transcription, mRNA processing, translation, translocation, and maturation of BLT2, and the phrase "inhibit(s) the intracellular signaling of BLT2" means to inhibit any step among the binding of LTB4 to BLT2, the activation of BLT2 and its intracellular signaling pathway to induce human cancer.

The nucleotide sequence of human BLT2 gene is available at the NCBI (NM_019839) and denoted as SEQ ID NO: 1 in this specification. The BLT2 gene has 2 kinds of CDS form, long form CDS (1618-2787) and short form CDS (1711-2787), of which base sequences are denoted as SEQ ID NO: 2 and SEQ ID NO: 4. The amino acid sequence of the long form BLT2 protein is available at the NCBI (NM_019839) and denoted as SEQ ID NO: 3. The amino acid sequence of the long form BLT2 protein is available at the NCBI (AB029892) and denoted as SEQ ID NO: 5.

In a preferred embodiment, the substance may be a compound that binds to BLT2 and inhibits the intracellular signaling of BLT2. The compound is also referred to as BLT2 antagonist, which means a compound that antagonizes an action of LTB4 on BLT2. The compound can be screened according to the present screening method from the commercially available chemical DB.

In a preferred embodiment, the compound may be LY255283 (1-[5-ethyl-2-hydroxy-4-[[6-methyl-6-(1H-tetrazol-5-yl)heptyl]oxy]phenyl]-ethanone). FIG. 1a shows a chemical structure of LY255283. LY255283 is a competitive antagonist of the BLT2 receptor. LY255283 have been known to inhibit eosinophil chemotaxis by 80% at a concentration of 10 μM, and inhibits the binding of radiolabeled LTB4 to eosinophil membranes with an IC50 of 260 nM [*Ann N Y Acad Sci* 629 274-287 (1991)]. Also, LY255283 have been known to be a novel leukotriene B4 receptor antagonist, which limits activation of neutrophils and prevents acute lung injury induced by endotoxin in pigs [*Surgery*. 1993 August; 114(2): 191-8]. However, the anti-cancer activity of LY25583 was revealed by the present inventors for the first time.

In a preferred embodiment, the substance may be an antibody to BLT2 that inhibits the intracellular signaling of BLT2. The antibody binds to BLT2 competitively with LTB4, so that can inhibit the intracellular signaling of BLT2. The antibody can be produced according to the conventional methods for producing polyclonal or monoclonal antibody by using BLT2 or its fragment as an antigen.

In a preferred embodiment, the substance may be an antisense or siRNA oligonucleotide that inhibits the expression of BLT2. The antisense or siRNA oligonucleotide has a base sequence complementary to the nucleotide sequence of BLT2 mRNA as set forth in SEQ ID NO: 2.

The term "antisense oligonucleotide" used herein is intended to refer to nucleic acids, preferably, DNA, RNA or its derivatives, that are complementary to the base sequences of a target mRNA, characterized in that they binds to the target mRNA and interfere its translation to protein. The antisense oligonucleotide of this invention means DNA or RNA sequences complementary and binding to BLT2 mRNA, that are able to inhibit translation, translocation, maturation or other biological functions of BLT2 mRNA. The antisense nucleic acid is 6-100, preferably, 8-60, more preferably, 10-40 nucleotides in length.

The antisense oligonucleotide may comprise at lease one modification in its base, sugar or backbone for its higher inhibition efficacy (De Mesmaeker et al., *Curr Opin Struct Biol.,* 5(3):343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA,* 86:6553 (1989)), cholic acid (Manoharan et al. *Bioorg. Med. Chem. Let.,* 4:1053 (1994)), a thioether, e.g., hexyl-S-tritylthiol (Manoharan et al. *Ann. N.Y. Acad. Sci.,* 660:306 (1992); Manoharan et al. *Bioorg. Med. Chem. Let.,* 3: 2765 (1993)), a thiocholesterol (Oberhauser et al., *Nucl. Acids Res.,* 20:533 (1992)), an aliphatic chain, e.g., dodecandiol or undecyl residues (Saison-Behmoaras et al. *EMBO J.,* 10:111 (1991); Kabanov et al. *FEBS Lett.,* 259:327 (1990); Svinarchuk et al. *Biochimie,* 75:49 (1993), a phospholipid, e.g., di-hexadecyl-rac-glycerol or triethylammonium 1,2-di-O-hexadecyl-rac-glycero-3-H-phosphonate (Manoharan et al. *Tetrahedron Lett.,* 36:3651 (1995); Shea et al. *Nucl. Acids Res.,* 18:3777 (1990)), a polyamine or a polyethylene glycol chain (Manoharan et al. *Nucleosides & Nucleotides,* 14:969 (1995)), or adamantane acetic acid (Manoharan et al. *Tetrahedron Lett,* 36: 3651 (1995)). Oligonucleotides comprising lipophilic moieties, and methods for preparing such oligonucleotides are known in the art, for example, U.S. Pat. Nos. 5,138,045, 5,218,105 and 5,459,255. The modifications described above enhance stability against nuclease degradation and increase affinity of the antisense oligonucleotide toward its target mRNA.

The antisense molecule is conventionally synthesized in vitro and then transmitted to cells. In addition, it is intracellularly produced by transcription from foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to peptide.

According to a preferred embodiment, the antisense oligonucleotide may have a base sequence of SEQ ID NO: 6, which is complementary to the target region (1738-1752) of SEQ ID NO: 2.

According to a preferred embodiment, the siRNA oligonucleotide may have a sense sequence of SEQ ID NO: 7 and an antisense sequence of SEQ ID NO: 8, which is complementary to the target region (1705-1724) of SEQ ID NO: 2.

The term "siRNA" used herein refers to a nucleic acid molecule mediating RNA interference or gene silencing (see WO 00/44895, WO 01/36646, WO 99/32619, WO 01/29058, WO 99/07409 and WO 00/44914). The siRNA to inhibit expression of a target gene provides effective gene knockdown method or gene therapy method. It was been first in plants, insects, Drosophila melanogaster and parasites and recently has been used for mammalian cell researches.

The siRNA molecule of this invention may consist of a sense RNA strand (having sequence corresponding to BLT2 mRNA) and an antisense RNA strand (having sequence complementary to BLT2 mRNA) and form a duplex structure. Alternatively, the siRNA molecule of this invention may have a single strand structure comprising self-complementary sense and antisense strands.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably, 15-80 nucleotides, and more preferably, 20-70 nucleotides.

The siRNA may comprise either blunt or cohesive end so long as it enables to silent the BLT2 expression due to RNAi effect. The cohesive end may be prepared in 3'-end overhanging structure or 5'-end overhanging structure.

The siRNA may be constructed by inserting a short nucleotide sequence (e.g., about 5-15 nt) between self-complementary sense and antisense strands. The siRNA expressed forms a hairpin structure by intramolecular hybridization, resulting in the formation of stem-and-loop structure. The stem-and-loop structure is processed in vitro or in vivo to generate active siRNA molecule mediating RNAi.

In the preferred embodiment, the substance may be a compound that inhibits the upstream or downstream signaling pathway of BLT2.

In the preferred embodiment, the human cancer may be any cancer that is induced by over-expression of BLT2 protein or oncogenic Ras. The present inventors have found that BLT2 protein was over-expressed in bladder cancer, breast cancer, prostate cancer, liver cancer, brain cancer, skin cancer, etc. and that the inhibition of the over-expression of BLT2 can suppress cancer transformation. Therefore, any anti-cancer therapy strategy based on the inhibition of BLT2 overexpression is claimed as the present invention.

In the preferred embodiment, the human cancer may be selected from the group consisting of bladder, prostate, pancreatic, and breast cancer. The present inventors demonstrated that the present BLT2 inhibitors have the anti-cancer effects against bladder, prostate, pancreatic, and breast cancer in Examples.

In the preferred embodiment, the treatment of human cancer may be accomplished by inducing the apoptosis of cancer cells, inhibiting the metastasis of cancer cells, or inhibiting the angiogenesis of tumor.

Therefore, any use of BLT2 inhibitors as apoptosis-inducing therapeutic composition against human cancer cells is claimed in the present invention. The present inventors have found that BLT2 antagonist LY255283 has an apoptosis-inducing activity against bladder, prostate, pancreatic, and breast cancer in Examples. Further, any use of BLT2 inhibitors as cancer cell metastasis-inhibiting therapeutic composition is claimed in the present invention. The present inventors have found that treatment of BLT2-signaling inhibitor LY255283 or BLT2 anti-sense oligonucleotide remarkably suppresses the metastasis of cancer cells induced by over-expression of oncogenic Ras in mouse. Further, any use of BLT2 inhibitors as tumor angiogenesis-inhibiting therapeutic composition is claimed in the present invention. The present inventors have found that BLT2 antagonist LY255283 or BLT2 antisense oligonucleotide remarkably suppresses a tumor angiogenesis.

According to another aspect of the present invention, there is provided a use of a combination of (a) a substance that inhibits the expression or intracellular signaling of BLT2, and (b) other anti-cancer drugs for the manufacture of a medicament for the treatment of human cancer.

In a preferred embodiment, the combination of BLT2 antagonist LY255283 and epirubicin may be used for the manufacture of a medicament for the treatment of breast cancer. The epirubicin is an anthracycline drug used for chemotherapy. The epirubicin is primarily used against breast and ovarian cancer, gastric cancer, lung cancer, and lymphomas. The present inventors have found that a combined use of BLT2 antagonist LY255283 and a conventional anti-cancer drug epirubicin represents remarkable and synergetic anti-cancer effects against breast cancer.

In a preferred embodiment, the combination of BLT2 antagonist LY255283 and androgen receptor antagonist may be used for the manufacture of a medicament for the treatment of prostate cancer. It is well known that the androgen receptor antagonist, such as bicalutamide, has an anti-cancer activity against human prostate cancer [Biochemical and Biophysical Research Communications, Vol. 357, No. 2, 341-346, 2007]. Many kinds of androgen receptor antagonist is available, for example 6-sulfonamido-quinolin-2-one and 6-sulfonamido-2-oxo-chromene derivatives (U.S. Pat. No. 7,064,207). Therefore, the combined use of BLT2 antagonist LY255283 and an androgen receptor antagonist may represents synergetic anti-cancer effects against prostate cancer.

According to another aspect of the present invention, there is provided a pharmaceutical composition for the treatment of human cancer, which comprises a substance that inhibits the expression or intracellular signaling of BLT2 as an active ingredient. In the pharmaceutical composition of the present invention, the substance may be chemical compounds, peptides, antibody proteins, nucleotides, antisense oligonucleotides, siRNA oligonucleotides or extract of natural source. The present pharmaceutical composition may comprise a pharmaceutically acceptable carrier in addition.

According to another aspect of the present invention, there is provided a pharmaceutical composition for the treatment of human cancer, which comprises a combination of (a) a substance that inhibits the expression or intracellular signaling of BLT2 and (b) other anti-cancer drugs as active ingredients. The other anti-cancer drugs may be any conventional anti-cancer drugs known to be effective to the corresponding cancers.

According to another aspect of the present invention, there is provided a method for treating a patient with cancer, which comprises administering a therapeutically effective amount of a substance that inhibits the expression or intracellular signaling of BLT2 to the patient.

According to another aspect of the present invention, there is provided a method for treating a patient with cancer, which comprises administering a therapeutically effective amount of (a) a substance that inhibits the expression or intracellular signaling of BLT2 and (b) other anti-cancer drugs to the patient. According to another aspect of the present invention, there is provided a method for screening a substance for treating human cancer, which comprises the steps of:
(a) contacting the substance to be analyzed to a cell containing BLT2 gene or protein; and,
(b) measuring the expression or intracellular signaling level of BLT2, wherein if the expression or intracellular signaling level of BLT2 is down-regulated, the substance is determined to have a potency to treat human cancer.

According to the present method, the cell containing the BLT2 gene or protein can be easily prepared by obtaining cells containing their original BLT2 gene or by transfecting cells with a foreign BLT 2 gene. Preferably, the cells containing the BLT2 gene or protein are transformed cancer cells. The cells are first contacted to substances to be analyzed. The term "substance" used herein in conjunction with the present screening method refers to a material tested in the present method for analyzing the influence on the expression level of the BLT2 gene, the amount of the BLT2 protein or the intracellular signaling level of the BLT2 receptor. The substance includes chemical compounds, peptides, antibody proteins, nucleotides, antisense-RNA, siRNA (small interference RNA) and extract of natural source, but not limited to.

Afterwards, the expression level of the BLT2 gene, the amount of the BLT2 protein or the intracellular signaling level of the BLT2 receptor in cells is measured. Where the expression level of the BLT2 gene, the amount of the BLT2 protein or the intracellular signaling level of the BLT2 receptor is measured to be down-regulated, the substance is determined to be a candidate to treat human cancers.

The measurement of the expression level of the BLT2 gene could be carried out by a variety of methods known in the art. For example, RT-PCR (Sambrook et al., *Molecular Cloning. A Laboratory Manual*, 3rd ed. Cold Spring Harbor Press (2001)), Northern blotting (Peter B. Kaufma et al., *Molecular and Cellular Methods in Biology and Medicine*, 102-108, CRC press), hybridization using cDNA microarray (Sambrook et al., *Molecular Cloning. A Laboratory Manual*, 3rd ed. Cold Spring Harbor Press (2001)) and in situ hybridization (Sambrook et al., *Molecular Cloning. A Laboratory Manual*, 3rd ed. Cold Spring Harbor Press (2001)) may be used.

Where the expression level of the BLT2 gene is analyzed by RT-PCT, total RNA is first isolated from cells treated with a substance to be analyzed and a first cDNA strand is then synthesized using oligo dT primer and reverse transcriptase. Then, PCR amplifications are performed using the first cDNA strand as templates and a BLT2-specific primer set. Finally, the PCR amplified products are resolved by electrophoresis and bands are analyzed for assessing the expression level of the BLT2 gene.

The amount of the BLT2 protein may be determined by various immunoassays known in the art. For example, radioimmunoassay, radioimmuno-precipitation, enzyme-linked immunosorbent assay (ELISA), capture-ELISA, inhibition or competition assay and sandwich assay are used for analyzing the amount of the BLT2 protein.

The intracellular signaling level of the BLT2 receptor may be determined by monitoring an event induced by LTB4, e.g., monitoring the rise of the intracellular calcium concentration as described in example using BLT2-expressing cells etc. (e.g., BLT2 overexpressing cells etc.). For example, if the substance reduces the intracellular calcium concentration by LTB4 in BLT2-expressing cells, it can be judged as BLT2 antagonist.

According to another aspect of the present invention, there is provided a kit for detecting human cancer, which comprises a primer or probe having a base sequence complementary to the base sequence of BLT2 gene as set forth in SEQ ID NO: 2. Therefore, any methodology or kit developed based on the information that BLT2 overexpression is detected at various human cancer may be included in the present invention.

The probes or primers used in the present kit has a complementary sequence to the nucleotide sequence of the BLT2 gene. The term "complementary" with reference to sequence used herein refers to a sequence having complementarity to the extent that the sequence anneals or hybridizes specifically with the nucleotide sequence of the BLT2 gene under certain annealing or hybridization conditions. In this regard, the term "complementary" used herein has different meaning from the term "perfectly complementary". The probes or primers used in the present invention can be one or more mismatch, so long as such mismatches are not sufficient to completely preclude specific annealing or hybridization to the BLT2 gene.

As used herein the term "probe" means a linear oligomer of natural or modified monomers or linkages, including deoxyribonucleotides and ribonucleotides, capable of specifically binding to a target polynucleotide. The probe may be naturally occurring or artificially synthesized. The probe is preferably single stranded. Preferably, the probes used in the present invention are oligodeoxyribonucleotides. The probe of this invention can be comprised of naturally occurring dNMP (i.e., dAMP, dGM, dCMP and dTMP), modified nucleotide, or non-natural nucleotide. The primer can also include ribonucleotides. For instance, the probes of this invention may include nucleotides with backbone modifications such as peptide nucleic acid (PNA) (M. Egholm et al., *Nature*, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The suitable length of primers will depend on many factors, including temperature, application and source of primer, generally, 15-30 nucleotides in length. Shorter primers generally need lower temperature to form stable hybridization duplexes to templates.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the BLT2 gene as templates; it is sufficient that they have complementarity to the extent that they anneals specifically to the nucleotide sequence of the BLT2 gene for acting as a point of initiation of synthesis. The primer design may be conveniently performed with referring to the BLT2 gDNA or cDNA sequences, preferably, cDNA sequence. For instance, the primer design may be carried out using computer programs for primer design (e.g., PRIMER 3 program). Exemplified primers of this invention is set forth in SEQ ID NO: 9 (sense primer) and SEQ ID NO: 10 (antisense primer).

According to a preferred embodiment, the diagnosis or detection kit for human cancers comprising probes is in the form of microarray, more preferably DNA or cDNA microarray, most preferably cDNA microarray.

In microarray, the present probes serve as hybridizable array elements and are immobilized on substrates. A preferable substrate includes suitable solid or semi-solid supporters, such as membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxi compound or aldehyde group or to a polylysin-coated surface. Further, the hybridizable array elements are bound to a substrate through linkers (e.g. ethylene glycol oligomer and diamine).

DNAs to be examined with a microarray of this invention may be labeled, and hybridized with array elements on microarray. Various hybridization conditions are applicable, and for the detection and analysis of the extent of hybridization, various methods are available depending on labels used.

The present method for diagnosing human cancer may be carried out in accordance with hybridization. For such analysis, probes, which have a complementary sequence to the nucleotide sequence of the BLT2 gene, are used.

Using probes hybridizable with the BLT2 gene or cDNA, preferably cDNA, human cancer is diagnosed or detected by hybridization-based assay. According to a preferred embodiment, some modifications in the probes of this invention can be made unless the modifications abolish the advantages of the probes. Such modifications, i.e., labels linking to the probes generate a signal to detect hybridization. Suitable labels include fluorophores (e.g., fluorescein), phycoerythrin, rhodamine, lissamine, Cy3 and Cy5 (Pharmacia), chromophores, chemiluminescers, magnetic particles, radioisotopes (e.g., $P^{32}$ and $S^{35}$), mass labels, electron dense particles, enzymes (e.g., alkaline phosphatase and horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, *Methods in Enzymology,* 65:499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample (preferably, cDNA) to be analyzed may be prepared using mRNA from various biosamples. The biosample is preferably a cell from bladder, prostate, pancreatic or breast cancer. Instead of probes, cDNA may be labeled for hyribridization-based analysis.

Probes are hybridized with cDNA molecules under stringent conditions for detecting human cancers. Suitable hybridization conditions may be routinely determined by optimization procedures. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual,* Cold Spring Harbor Laboratory Press, Cold Spring Harbor, N.Y. (2001); and M. L. M. Anderson, *Nucleic Acid Hybridization,* Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine; a pair of alkaline phosphatase and bromochloroindolylphosphate (BCIP), nitro blue tetrazolium (NBT), naphthol-AS-B1-phosphate or ECF substrate; and a pair of glucosidase and t-NBT (nitroblue tetrazolium) or m-PMS (phenzaine methosulfate). Where probes are labeled with gold particles, the occurrence of hybridization may be detected by silver staining method using silver nitrate.

In these connections, where the present method for diagnosing human cancers is carried out by hybridization, it comprises the steps of (i) contacting a nucleic acid sample to a probe having a nucleotide sequence complementary to the nucleotide sequence of the BLT2 gene; and (ii) detecting the occurrence of hybridization.

The signal intensity from hybridization is indicative of human cancers. When the hybridization signal to BLT2 cDNA from a sample to be diagnosed is measured to be stronger than normal samples, the sample can be determined to have human cancers.

According to a preferred embodiment, the primers of this invention are used for amplification reactions.

The term used herein "amplification reactions" refers to reactions for amplifying nucleic acid molecules. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., *Molecular Cloning. A Laboratory Manual,* 3rd ed. Cold Spring Harbor Press (2001)), the methods of Miller, H. I. (WO 89/06700) and Davey, C. et al. (EP 329,822), ligase chain reaction (LCR) (17, 18), Gap-LCR (WO 90/01069), repair chain reaction (EP 439,182), transcription-mediated amplification (TMA) (19) (WO 88/10315), self sustained sequence replication (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification and loop-mediated isothermal amplification (LAMP), but not limited to. Other amplification methods that may be used are described in, U.S. Pat. Nos. 5,242,794, 5,494,810, 4,988,617 and in U.S. Ser. No. 09/854,317.

According to the most preferred embodiment, the amplification reaction is carried out in accordance with PCR (polymerase chain reaction) which is disclosed in U.S. Pat. Nos. 4,683,195, 4,683,202, and 4,800,159.

PCR is one of the most predominant processes for nucleic acid amplification and a number of its variations and applications have been developed. For example, for improving PCR specificity or sensitivity, touchdown PCR(24), hot start PCR(25, 26), nested PCR(2) and booster PCR(27) have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR have been suggested for certain applications. The details of PCR can be found in McPherson, M. J., and Moller, S. G. *PCR*. BIOS Scientific Publishers, Springer-Verlag New York Berlin Heidelberg, N.Y. (2000), the teachings of which are incorporated herein by reference in its entity.

Where the present method for diagnosing human cancers is carried out using primers, the nucleic acid amplification is executed for analyzing the expression level of the BLT2 gene. Because the present invention is intended to assess the expression level of the BLT2 gene, the level of the BLT2 mRNA in samples is analyzed.

Therefore, the present invention performs nucleic acid amplifications using mRNA molecules in samples as templates and primers to be annealed to mRNA or cDNA.

For obtaining mRNA molecules, total RNA is isolated from samples. The isolation of total RNA may be performed by various methods (Sambrook, J. et al., *Molecular Cloning. A Laboratory Manual*, 3rd ed. Cold Spring Harbor Press (2001); Tesniere, C. et al., *Plant Mol. Biol. Rep.*, 9:242 (1991); Ausubel, F. M. et al., *Current Protocols in Molecular Biology*, John Willey & Sons (1987); and Chomczynski, P. et al., *Anal. Biochem.* 162:156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (*PNAS USA*, 85:8998 (1988); Libert F, et al., *Science*, 244:569 (1989); and Sambrook, J. et al., *Molecular Cloning. A Laboratory Manual*, 3rd ed. Cold Spring Harbor Press (2001)). cDNA molecules synthesized are then amplified by amplification reactions.

The primers used for the present invention is hybridized or annealed to a region on template so that double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophilus* (Tth), *Thermus filiformis*, *Thermis flavus*, *Thermococcus literalis*, and *Pyrococcus furiosus* (Pfu).

When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

Annealing or hybridization in the present method is performed under stringent conditions that allow for specific binding between the primer and the template nucleic acid. Such stringent conditions for annealing will be sequence-dependent and varied depending on environmental parameters.

The amplified BLT2 cDNA molecules are then analyzed to assess the expression level of the BLT2 gene. For example, the amplified products are resolved by a gel electrophoresis and the bands generated are analyzed to assess the expression level of the BLT2 gene. When the expression level of the BLT2 gene from a sample to be diagnosed is measured to be higher than normal samples, the sample can be determined to have human cancers.

In these connections, where the present method for diagnosing human cancers is carried out by amplification, it comprises the steps of (i) amplifying a nucleic acid sample by use of a primer having a nucleotide sequence complementary to the nucleotide sequence of the BLT2 gene; and (ii) analyzing the amplified products to determine the expression level of the BLT2 gene.

In a preferred embodiment, the kit may comprise a pair of primers having a forward sequence of SEQ ID NO: 9 and a reverse sequence of SEQ ID NO: 10. This primer set can detect both of the long form and short form BLT2.

In a preferred embodiment, the kit may comprise a pair of primers having a forward sequence of SEQ ID NO: 11 and a reverse sequence of SEQ ID NO: 12. This primer set can detect only long form of BLT2 because the primer recognizes the front part of long form CDS.

According to another aspect of the present invention, there is provided a kit for detecting human cancer, which comprises an antibody binding specifically to BLT2 protein. The diagnosing kit for human cancer may be constructed by incorporating an antibody binding specifically to the BLT2 protein.

The antibody against the BLT2 protein used in this invention may polyclonal or monoclonal, preferably monoclonal. The antibody could be prepared according to conventional techniques such as a fusion method (Kohler and Milstein, European Journal of Immunology, 6:511-519 (1976)), a recombinant DNA method (U.S. Pat. No. 4,816,56) or a phage antibody library (Clackson et al, Nature, 352:624-628 (1991) and Marks et al, J. Mol. Biol., 222:58, 1-597 (1991)). The general procedures for antibody production are described in Harlow, E. and Lane, D., Antibodies: A Laboratory Manual, Cold Spring Harbor Press, New York, 1988; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991, which are incorporated herein by references. For example, the preparation of hybridoma cell lines for monoclonal antibody production is done by fusion of an immortal cell line and the antibody producing lymphocytes. This can be done by techniques well known in the art. Polyclonal antibodies may be prepared by injection of the BLT2 protein antigen to suitable animal, collecting antiserum containing antibodies from the animal, and isolating specific antibodies by any of the known affinity techniques.

Where the diagnosing method of this invention is performed using antibodies to the BLT2 protein, it could be carried out according to conventional immunoassay procedures for detecting human cancer.

Such immunoassay may be executed by quantitative or qualitative immunoassay protocols, including radioimmunoassay, radioimmuno-precipitation, enzyme-linked immunosorbent assay (ELISA), capture-ELISA, inhibition or competition assay, sandwich assay, flow cytometry, immunofluorescence assay and immuoaffinity assay, but not limited to. The immunoassay and immuostaining procedures can be found in *Enzyme Immunoassay*, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies: A Laboratory Manual*, Cold Spring Harbor Press, 1999, which are incorporated herein by references.

For example, according to the radioimmunoassay method, the radioisotope (e.g., $C^{14}$, $I^{125}$, $P^{32}$ and $S^{35}$) labeled antibody may be used to detect the BLT2 protein.

In addition, according to the ELISA method, the example of the present method may comprise the steps of: (i) coating a surface of solid substrates with cell lysate to be analyzed; (ii) incubating the coated cell lysate with a primary antibody to the BLT2 protein; (iii) incubating the resultant with a secondary antibody conjugated with an enzyme; and (iv) measuring the activity of the enzyme.

The solid substrate useful in this invention includes carbohydrate polymer (e.g., polystyrene and polypropylene), glass, metal and gel, most preferably microtiter plates.

The enzyme conjugated with the secondary antibody is that catalyzing colorimetric, fluorometric, luminescence or infrared reactions, e.g., including alkaline phosphatase, β-galactosidase, luciferase, Cytochrome $P_{450}$ and horseradish peroxidase. Where using alkaline phosphatase, bromochloroindolylphosphate (BCIP), nitro blue tetrazolium (NBT) or ECF may be used as a substrate for color-developing reactions; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

Where the present method is performed in accordance with the capture-ELISA method, the specific example of the present method may comprise the steps of: (i) coating a surface of a solid substrate with a capturing antibody capable of binding specifically to the BLT2 protein; (ii) incubating the capturing antibody with a cell sample to be analyzed; (iii) incubating the resultant of step (ii) with a detecting antibody which is capable of binding specifically to the BLT2 protein and conjugated with a label generating a detectable signal; and (iv) detecting the signal generated from the label conjugated with the detecting antibody.

The detecting antibody has a label generating a detectable signal. The label includes, but not limited to, a chemical (e.g., biotin), an enzymatic (e.g., alkaline phosphatase, horseradish peroxidase, β-galactosidase and Cytochrome $P_{450}$), a radioactive (e.g., $C^{14}$, $I^{125}$, $P^{32}$ and $S^{35}$), a fluorescent (e.g., fluorescein), a luminescent, a chemiluminescent and a FRET (fluorescence resonance energy transfer) label. Various labels and methods for labeling antibodies are well known in the art (Ed Harlow and David Lane, *Using Antibodies*, A Laboratory Manual, Cold Spring Harbor Laboratory Press, 1999).

The detection of the signal generated from the label conjugated with the detecting antibody can be carried out by various processes well known in the art. The detection of the signal enables to analyze the BLT2 protein in a quantitative or qualitative manner. Where biotin and luciferase are used as labels, the signal detection may be achieved by use of streptavidin and luciferin, respectively.

The measurement of signal intensities generated from the immunoassay described above is indicative of human cancer. When the signal to the BLT2 protein in a biosample to be diagnosed is measured to be higher than normal samples, the biosample can be determined to have human cancer.

The kit of the present invention may optionally include other reagents along with primers, probes or antibodies described above. For instance, where the present kit may be used for nucleic acid amplification, it may optionally include the reagents required for performing PCR reactions such as buffers, DNA polymerase (thermostable DNA polymerase obtained from *Thermus aquaticus* (Taq), *Thermus thermophilus* (Tth), *Thermus filiformis, Thermis flavus, Thermococcus literalis*, and *Pyrococcus furiosus* (Pfu)), DNA polymerase cofactors, and deoxyribonucleotide-5-triphosphates. The kits, typically, are adapted to contain in separate packaging or compartments the constituents afore-described.

The kits for detecting or diagnosing human cancer permit to determine the development, aggravation and alleviation of human cancer. In this regard, the term used herein "detecting or diagnosing" with reference to disease means not only the determination of the existence of disease but also the development, aggravation and alleviation of disease.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A pharmaceutical composition of this invention may be administered orally or parenterally (e.g., intravenous injection, subcutaneous injection, intramuscular injection and local injection).

The term "Therapeutically effective amount" as used herein means an amount of the substance that is capable of producing a medically desirable result in a treated subject. The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. According to a preferred embodiment of this invention, a daily suitable dosage unit for human host ranges from 0.001-100 mg/kg (body weight).

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

BRIEF DESCRIPTION OF THE DRAWINGS

The above object and advantages of the present invention will become more apparent by describing in detail preferred embodiments thereof with reference to the attached drawings in which.

BEST MODE FOR CARRYING OUT THE INVENTION

Practical and presently preferred embodiments of the present invention are illustrated as shown in the following Examples. However, it will be appreciated that those skilled in the art, on consideration of this disclosure, may make modifications and improvements within the spirit and scope of the present invention.

EXAMPLE 1

Figure 1A:
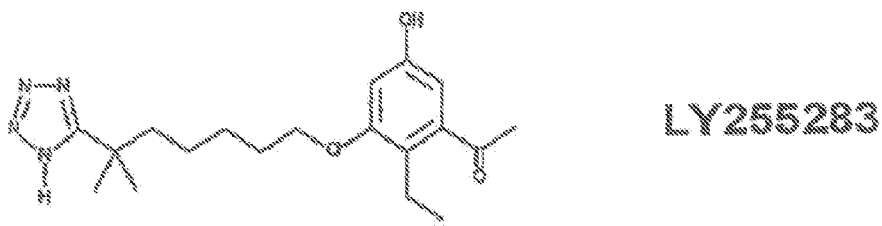
FIG. 1a shows a chemical structure of LY255283, a BLT2 antagonist.
Figure 1B:
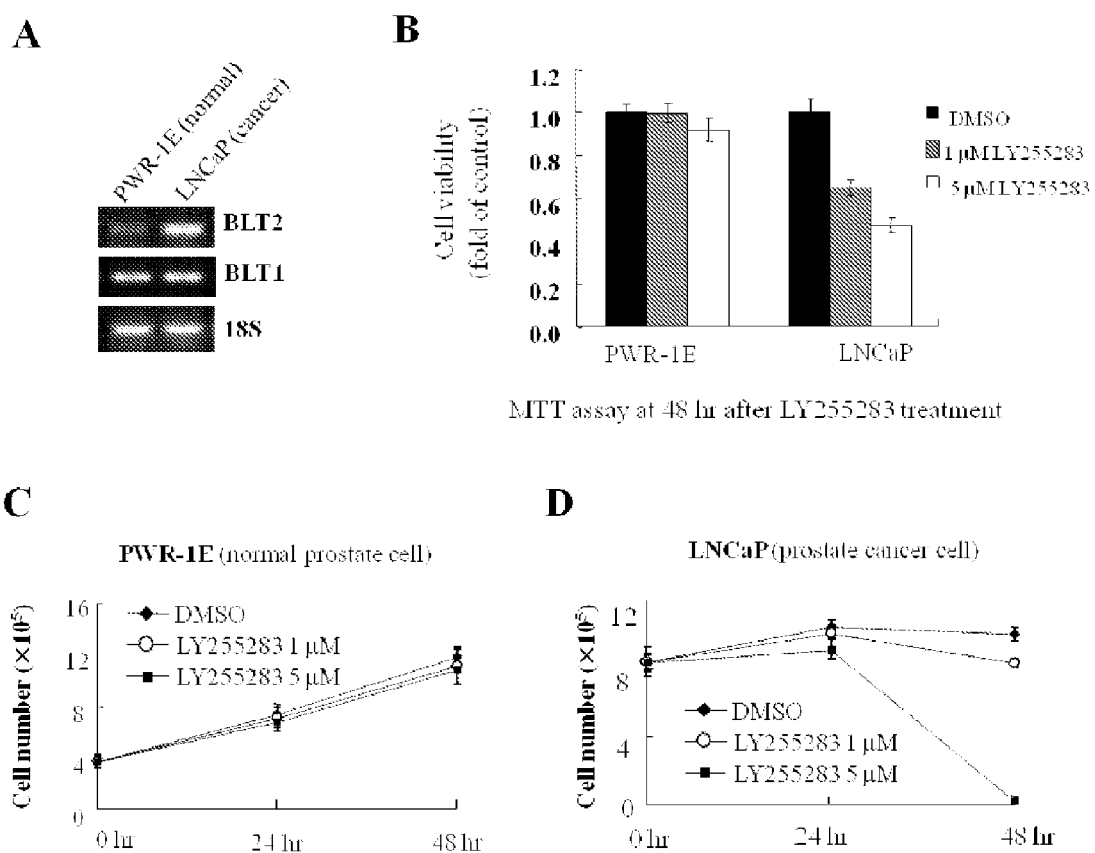
FIG. 1b shows the effect of BLT2 antagonist LY255283 on prostate cancer cell viability. The BLT2 antagonist significantly reduced prostate cancer cells viability.

BLT2 Antagonist Significantly Reduces Prostate Cancer Cells Viability (1) RT-PCR (A of FIG. 1b)

In prostate cancer cells and normal cells, BLT2 mRNA level was analyzed by RT-PCR. Total cellular RNA was extracted using Easy-Blue reagent (Intron Co.) and dissolved in diethylpyrocarbonate-treated water. 2 µg of RNA was reverse transcribed for 30 min at 45° C. and pre-denatured for 5 min at 94° C. in 20 µl in buffer containing 10 mM Tris (pH 8.3), 50 mM KCl, 5 mM $MgCl_2$, 1 mM each of dATP, dCTP, dGTP, and dTTP, and oligo(dT) primers. Then PCR reaction was performed as follows. For BLT1 and BLT2, samples denatured at 94° C. for 30 sec, annealed at 67° C. for 30 sec and extended at 72° C. for 30 sec for 33 repetitive cycles. For 18 s, samples were denatured at 94° C. for 30 sec, annealed at 55° C. for 30 sec and extended at 72° C. for 30 sec for 19 repetitive cycles. The products were separated by electrophoresis on 1.5% agarose gels and visualized with ethidium bromide staining. The primers, purchased from Genotech Inc. (Korea) were as follows. BLT1 forward: 5'-TAT GTC TGC GGA GTC AGC ATG TAC GC-3'; reverse: 5'-CCT GTA GCC GAC GCC CTA TGT CCG-3'); BLT2 forward: 5'-AGC CTG GAG ACT CTG ACC GCT TTC G-3', reverse: 5'-GAC GTA GAG CAC CGG GTT GAC GCT A-3'; 18 s forward: 5'-TTC GGA ACT GAG GCC ATG AT-3', reverse: 5'-TTT CGC TCT GGT CCG TCT TG-3'). The expression of housekeeping gene 18 s RNA was used to normalize for transcription and amplifications among samples. The result showed that the level of BLT2 mRNA was elevated in LNCaP cells, prostate cancer cells, as compared with PWR-1E, prostate normal epithelial cells.

(2) MTT assay (B of FIG. 1b)

The effect of LY255283, BLT2 antagonist, on cell viability was examined by MTT assay. PWR-1E cells were seeded at a density of $1.0 \times 10^4$ cells/well and LNCaP cells were seeded at a density of $1.5 \times 10^4$ cells/well in 96-well culture dishes. After 36 hr, the medium was replaced with serum free RPMI 1640 and cells were stimulated with DMSO or LY255283 of increasing concentration. MTT (1 mg/ml) was added at 48 hr after LY255283 treatment and after 4 hr of further incubation the medium was replaced with DMSO. Then cells were incubated at room temperature for 10 min. The spectrophotometric absorbance of the samples was determined by using Ultra Multifunctional Microplate Reader at 540 nm. LNCaP cells and PWR-1E cells were stimulated with LY255283 of various concentration in serum free RPMI1640. The treatment with LY255283 resulted in a dose dependent reduction of LNCaP cell viability with no effect on PWR-1E cells.

(3) Cell Counting (C and D of FIG. 1b)

The effect of LY255283 was observed by counting of cell number. The cells were grown in 6-well cluster dishes to 70% confluence with 10% FBS-supplemented medium. At day 0, the medium was replaced with serum free RPMI 1640 and cells were stimulated with DMSO or 1 µM and 5 µM LY255283. The cells were harvested at various intervals. Cells were washed with PBS and collected by brief trypsinization. Total cell number was determined by counting each sample in duplicate with a hemocytometer using trypan blue dye. The cells treated with LY255283 in serum free RPMI1640 were harvested at various intervals. The number of LNCaP cells was significantly reduced by LY255283, but not PWR-1E cells. These result indicated that the reduction of cell viability by LY255283 was significant in LNCaP cells which expressed elevated level of BLT2 mRNA. In contrast, PWR-1E cells which expressed few level of BLT2 were not affected by LY255283.

EXAMPLE 2

Figure 1C:
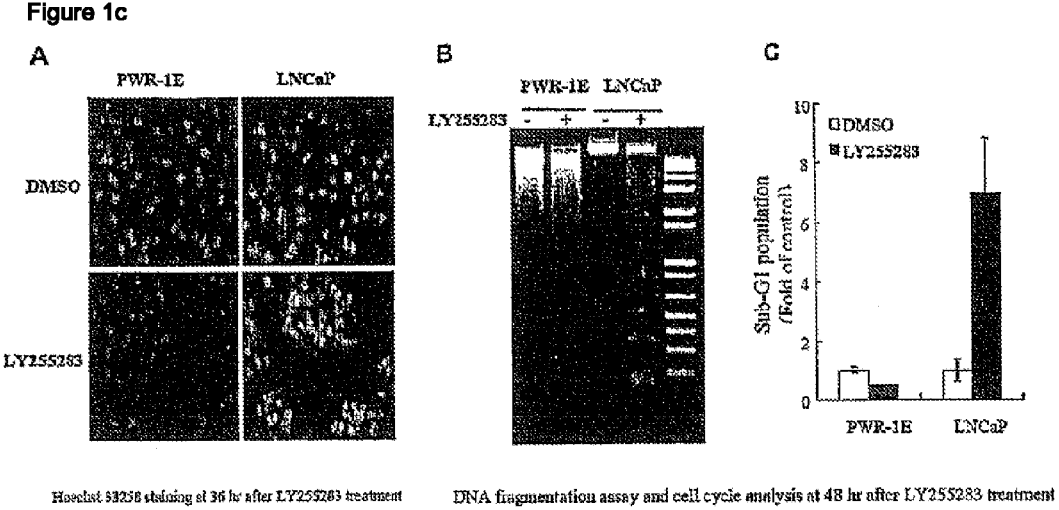
FIG. 1c shows the effect of BLT2 antagonist LY255283 on prostate cancer cell apoptosis. The BLT2 blockade induced apoptosis in prostate cancer cells.

Apoptosis Induced by BLT2 Blockade in Prostate Cancer Cells (1) Hoechst 33258 staining (A of FIG. 1c)

The cells grown in 6-well cluster dishes were stimulated with 5 µM LY255283 for 36 hr in serum free RPMI 1640. The cells were fixed for 10 min with 4% formaldehyde and stained with Hoechst 33258 (50 µg/ml) (Sigma) for 10 min at 37° C. and observed under fluorescence microscopy (Carl Zeiss). The neuclei condensation of fragmentation was observed in LY255283-treated LNCaP cells, but not PWR-1E cells.

(2) DNA Fragmentation Assay (B of FIG. 1c)

LNCaP and PWR-1E cells were treated with 5 µM LY255283 for 48 hr and DNA fragmentation assay was performed. DNA fragmentation was shown by the harvesting of total cellular DNA. Cells were grown in 10 cm plates to 70% confluence with 10% FBS-supplemented medium. Then the media was replaced with serum free RPMI 1640 and the cells were treated with 5 µM LY255283 for 48 hr. Cellular DNA from cells was extracted incubating with lysis buffer (1 mM EDTA, 10 mM Tris, 120 mM NaCl, 1% SDS and 100 µg/ml proteinase K, pH 8.0) for 12 hr at 50° C. The lysate was centrifuged for 10 min at 13,000×g to separate the fragment DNA. The supernatant was then extracted twice with phenol/chloroform/isoamyl alcohol and precipitated with absolute ethanol. The pellet was resuspended in Tris-EDTA and 10 mg/ml RNase A and the DNA was separated on a 1.8% agarose gel. After electrophoresis, gels were stained with ethidium bromide, and the DNA was visualized by UV light.

A smear of different sizes of DNA fragments was observed in LY255283-treated LNCaP cells.

(3) Cell Cycle Analysis (C of FIG. 1c)

After LNCaP cells and PWR-1E cells were treated with 5 µM LY255283 for 48 hr, the cells were fixed with 70% ethanol and stained with PI. Cell cycle was analyzed using flow cytometry. The cells grown in 6-well cluster dishes were stimulated with 5 µM LY255283 for 48 h in serum free RPMI 1640. The cells which were collected by brief trypsinization were fixed for 12 hr with 70% ethanol at 4° C. The cells were resuspended in PBS containing RNase A (100 µg/ml) and incubated for 30 min at 37° C. The cells were stained with propidium iodide (50 µg/ml) (Sigma). Acquisition and analysis was performed by FACS using Cell Quest Alias software (BD Bioscience). The graph showed the relative fold of sub-G1 population in LY255283-treated LNCaP and PWR-1E cells. The increased population of cells with sub-G1 DNA content was detected in LY255283-treated LNCaP cells. The various methods for the measurement of apoptosis showed similar results, suggesting that LY255283 induce apoptosis in prostate cancer LNCaP cells, but not prostate normal cells. In prostate cancer and normal cells, the differential effect on LY255283-induced apoptosis suggested that BLT2 play an important role in survival of prostate cancer cells which expressed elevated level of BLT2.

FIG. 1c showed that the LY255283-induced cell death was involved in apoptosis concomitantly. The apoptotic cells were detected by staining of fragmented nuclei by Hoechst33258 and PI and DNA fragmentation assay.

EXAMPLE 3

Figure 1D:
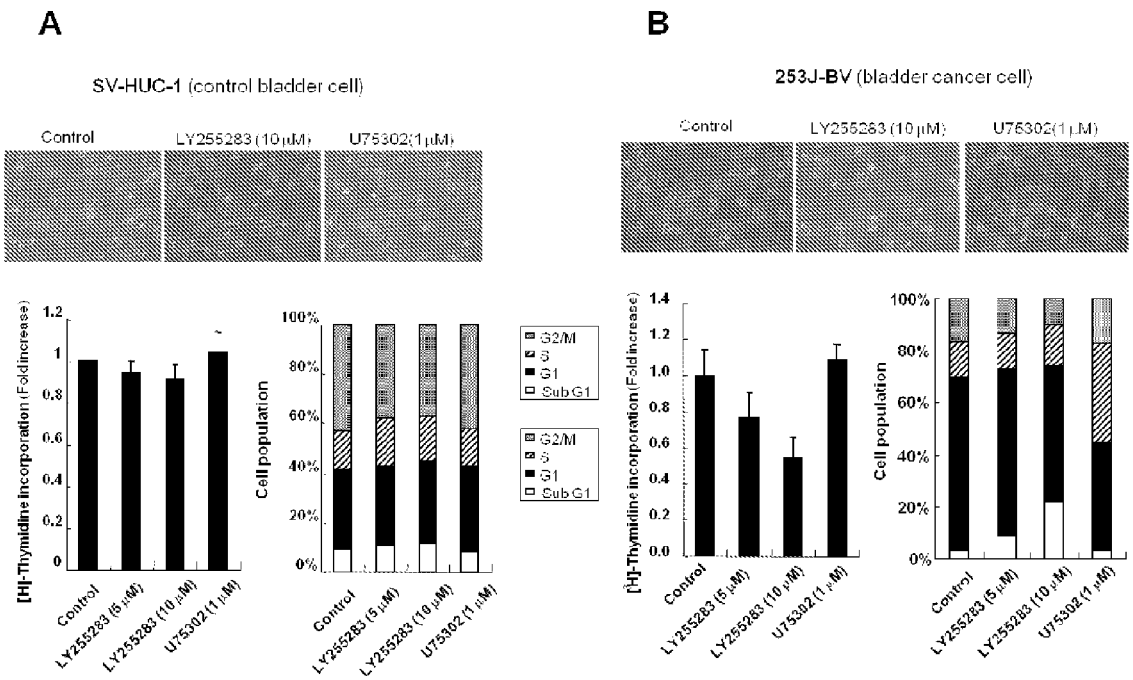
FIG. 1d shows the effect of BLT2 antagonist on bladder cancer cell cycle and apoptosis. The LY255283 induced cell cycle arrest in sub-G1 phase and apoptosis of bladder cancer cells.

LY255283 Induces Cell Cycle Arrest in Sub-G1 Phase and Apoptosis of Bladder Cancer Cells (1) Morphological Changes Using Light Microscopy (A and B of FIG. 1d)

Bladder cancer cells grown in 6 well-plate were treated with 10 uM LY255283, 1 uM U75302 for 48 hr. Cells were then viewed using light microscopy (×100). SV-HUC-1 cell (normal bladder cell) and 253J-BV cell (bladder cancer cell) were treated with different concentrations (1~10 µM) of LY255283 (BLT2 specific antagonist), U75302 (BLT1 specific antagonist) for 48 hr. As shown in FIGS. A and B of FIG. 1d, 253J-BV cells exhibited membrane blebbing, detached from plate treated only LY255283. But normal bladder cell line was not effect on morphological change treated with BLT antagonists.

(2) [$^3$H]-Thymidine Incorporation Assay (A-B Bottom Left Panel of FIG. 1d)

Cells were seed in 96-well plate at the density of $1.0 \times 10^4$/well. After 24 hr incubation in RPMI 1640 supplemented with 10% FBS, the media was replaced with RPMI 1640 containing 0.5% FBS for 12 hr. After cells were treated with different concentration BLT antagonists. Then [$^3$H]-thymidine (1 µCi/ml) (PerkinElmer Life Sciences) was added at 12 hr after antagonists treatment and after 36 hr of further incubation, cells were harvested on the filtermat (PerkinElmer Life Science) and filtermat was dried and packaged in the sample bag (PerkinElmer Life Science). Finally, Betaplate scint (PerkinElmer Life Science) was added to the filtermat, and the radioactivity was counted in a liquid scintillation counter (MicroBeta, Wallac/PerkinElmer). The specific LTB4 receptor 2 antagonist LY255283 caused a concentration dependent inhibition of thymidine incorporation in 253J-BV cells, but not SV-HUC-1 cells. LY255283 inhibited proliferation by at least 50% at a concentration of 10 µM at 48 hr.

(3) Cell Cycle Analysis (A-B Bottom Right Panel of FIG. 1d)

The cells grown in 6-well plate were stimulated with 5 μM and 10 μM LY255283, 1 μM U75302 for 48 h in RPMI 1640 containing 0.5% FBS. The cells which were collected by brief trypsinization were fixed overnight with 70% ethanol at 4° C. The cells were resuspended in PBS containing RNase A (100 μg/ml) and incubated for 30 min at 37° C. The cells were stained with propidium iodide (50 μg/ml) (Sigma). Acquisition and analysis was performed by FACS using Cell Quest Alias software (BD Bioscience). Similar effects were seen in the cell cycle progression. Cells were treated with BLT antagonist for 48 hours and the cell cycle population was measured by flow cytometry. In brief, cells were plated in 6 well plate and then treated with LY255283, U75302 for 48 hr. At the end of the treatment, the cells were harvested and then centrifuged. The cells fixed in ice-cold 70% ethanol for 24 hr and centrifuged. The pellet were resuspended in 0.5 ml phosphate-buffered saline (PBS) and incubated with PI 1 mg/ml treatment for 15 min. LY255283 inhibited cell growth by arresting cell cycle at sub-G1 in dose dependent manner.

LTB4 receptor 1 specific antagonist U75302 was not effect on cell proliferation and cell cycle in both SV-HUC-1 and 253J-BV cells. Then LY255283 10 μM and U75302 1 μM, these concentration only effect on bladder cancer cell line 253J-BV, was used for further studied.

EXAMPLE 4

LY255283 Induces Apoptosis and Loss of Mitochondrial Membrane Potential in 253J-BV Bladder Cancer Cell A selective BLT2 antagonist LY255283 has been shown to inhibit proliferation and induced cell death of human bladder cancer cells. We further studied whether the LY255283-induced cell death was apoptosis or not.

Figure 1E:
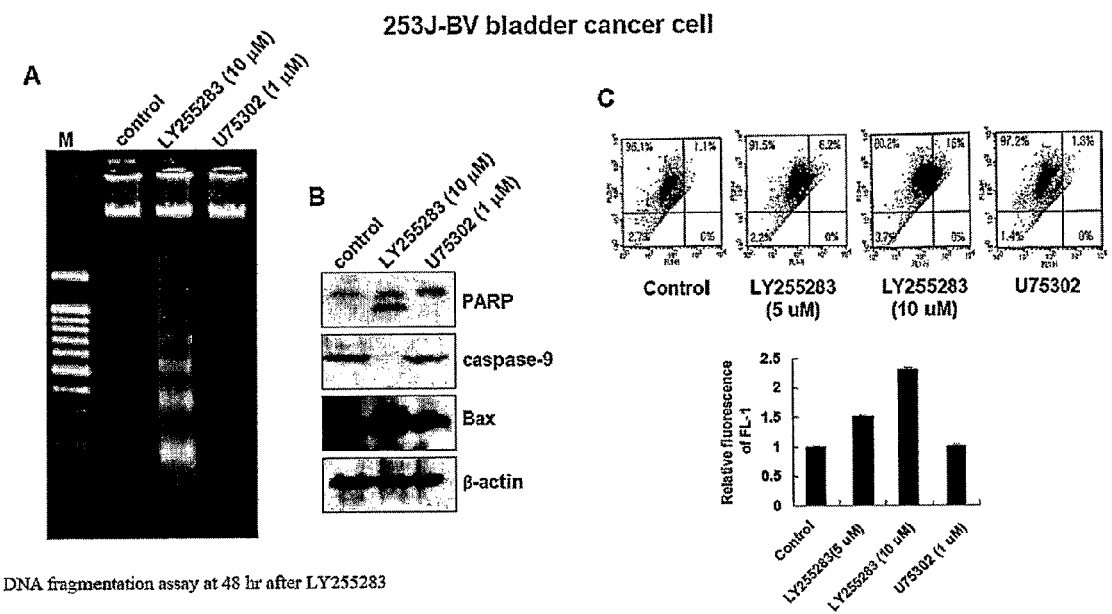
FIG. 1e shows the effect of BLT2 antagonist LY255283 on bladder cancer cell apoptosis. The LY255283 induced apoptosis and loss of mitochondrial membrane potential in 253J-BV bladder cancer cell.

(1) DNA Fragmentation (A of FIG. 1e)

DNA fragmentation was shown by the harvesting of total cellular DNA. Cells were grown in 100 mm plates to 80% confluence with 10% FBS-supplemented medium. Then the media was replaced with RPMI 1640 with 0.5% FBS and the cells were treated with 10 μM LY255283 and 1 μM for 48 hr. Cellular DNA from cells extracted incubating with lysis buffer (1 mM EDTA, 10 mM Tris, 120 mM NaCl, 1% SDS and 100 μg/ml proteinase K, pH 8.0) for 12 hr at 50° C. The lysate was centrifuged for 10 min at 13,000×g to separate the fragment DNA from intact chromatin (nuclear pellet). The supernatant was then extracted twice with phenol/chloroform/isoamyl alcohol and precipitated with absolute ethanol. The pellet was resuspended in Tris-EDTA and 10 mg/ml RNaseA and the DNA was separated on a 1.8% agarose gel. After electrophoresis, gels were stained with ethidium bromide, and the DNA was visualized by UV light. Apoptosis is characterized by fragmentation of chromosomal DNA. We investigated the effect of BLT antagonists on DNA damage of bladder cancer cell line. As expected, cells treated with LY255283 for 48 hr was observed a ladder like pattern of DNA fragments. In contrast, the control cell and treated U75302 cell not observed DNA fragments.

(2) Western Blot (B of FIG. 1e)

Cells were washed with cold PBS and cells were scraped into lysis buffer [20 mM Tris-HCl (pH 7.5), 150 mM NaCl, 0.5% NP-40, 5 mM EDTA, 1% triton X-100 added protease inhibitors] at 4° C. Harvested protein samples were heated at 95° C. for 5 min and then subjected to SDS-PAGE on acrylamide gels, followed by transfer to polyvinylidene difluoride membranes for 90 min at 100 V. The membranes were blocked for 1 h with Tris-buffered saline (TBS) containing 0.05% (vol/vol) Tween 20 plus 5% (wt/vol) nonfat dry milk and then incubated with appropriate antibodies (PARP, 1:2000 dilution, Caspase-9, 1:2000 dilution, Bax 1:2000 dilution, actin, 1:3000 dilution) in 5% nonfat milk overnight at 4° C. Then membrane bound protein-antibody complex incubated for 2 hr with HRP-conjugated secondary antibody before development with an enhanced chemiluminescence kit (Amersham Biosciences, UK). The poly ADP-ribose polymerase (PARP) cleavage have been well established as important indices of apoptosis. Apoptosis induction was observed in 253J-BV cell line after 48 hr LY255283 treatment. Western blot analysis showed that LY255283 caused a reduction of pro-caspase 9. These result indicate that LY255283 induced apoptosis was caspase dependent manner. And pro-apoptotic protein, Bax, was significant increased when cells were treated with 10 μM LY255283 for 48 hr. However, there was no significant change in the level of protein in cells treated with U75302 compared with control.

(3) Measurement of Mitochondrial Membrane Potential (C of FIG. 1e)

Mitochondrial damage is important to the apoptosis affected by the caspase-9 pathway. To evaluate the effect of LY255283 on the mitochondria membrane potential (MMP), cell were pretreated with the fluorescent mitochondria specific cationic dye, JC-1, and changes in membrane potential were measured by flow cytometry. Cells grown in 6 wellplates for 24 hr washed PBS and incubated in RPMI 1640 with 0.5% FBS containing different concentrations of LY255283 and 075302 for 48 hr. After cells were treated with 5 ug/ml of JC-1 for 30 min. Then removal of JC-1, washed with PBS, harvested by trypsinization, and resuspended in PBS. Sample was measured at 530 nm (FL-1 green) and 590 nm (FL-2 red) using a flow cytometry. LY255283 led to a drop in mitochondria potential after 48 hr of treatment at a concentration of 10 μM. LY255283 treatment increased green fluorescence (FL-1) about 2.5 fold compare with control cells. These result that LY255283 induced apoptosis might be linked to mitochondrial function and membrane permeability. And because of the loss of mitochondrial membrane potential in a LY255283 treated cells, it was speculated that caspase may play an essential role in the process of apoptosis.

EXAMPLE 5

LY255283 Induces Apoptosis in Pancreatic Cancer Cells (Panc-1 & AsPC-1)

To investigate the effect of the selective BLT2 antagonist LY255283 on pancreatic cancer cell proliferation and survival, we determined cell viability by MTT assay after Panc-1 and AsPC-1 cells were exposed to LY255283 for 48 h.

(1) Human Pancreatic Cancer Cell Lines and Cell Culture

Two human pancreatic cancer cell lines were used: Panc-1 and AsPC-1. Panc-1 cells were grown in DMEM, and AsPC-1 cells were grown in RPMI 1640. Cells were plated as monolayers in the medium supplemented with 10% heat inactivated FBS, 100 units/ml penicillin, and 100 μg/ml streptomycin at 37'C under a humidified 95%/5% (v/v) mixture of air and $CO_2$.

Figure 1F:
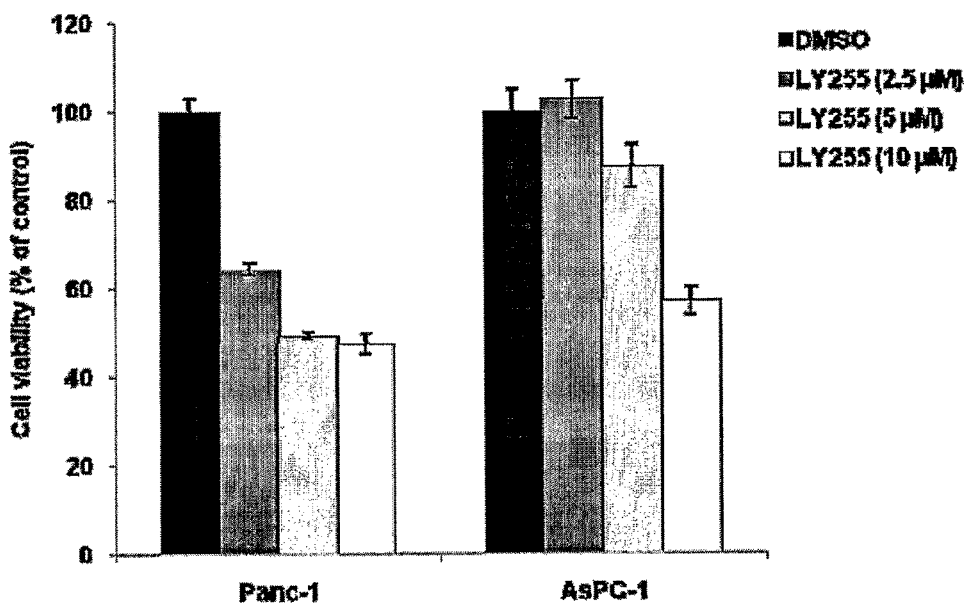
FIG. 1f shows the effect of BLT2 antagonist LY255283 on pancreatic cancer cell apoptosis. The LY255283 induced apoptosis in pancreatic cancer cells (Panc-1 & AsPC-1).

(2) MTT Assay (FIG. 1f)

Cells were plated in 96-well plates at a concentration of 10,000 cells/well. After incubation for 24 h, cells were serum-starved for 3 h, and then various concentrations (2.5 μM, 5 μM and 10 μM) of LY255283 were added. At the end of experiments, 25 μl of a 5 mg/ml MTT solution, diluted in PBS, was added into the 96-well plates. The plates were incubated at 37° C. in 5% $CO_2$ atmosphere for 3 h, allowing viable cells to reduce the yellow tetrazolium salt (MTT) into dark blue formazan crystals. At the end of the 3 h incubation, the MTT solution was removed and 100 μl of dimethyl sulfoxide was added to dissolve the formazan crystals. To ensure complete dissolution of the formazan crystals, the plates were vortexed gently at low speed for 10 min. The absorbance in individual wells was determined at 540 nm by a microplate reader.

The BLT2 antagonist LY255283 reduced a significant cell viability in pancreatic cancer cells in a dose-dependent manner in both Panc-1 and AsPC-3 cells at 48 h relative to control cells. LY255283 diminished cell viability in dose-dependent manner in both Panc-1 and AsPC-3 cells.

EXAMPLE 6

Figure 1G:
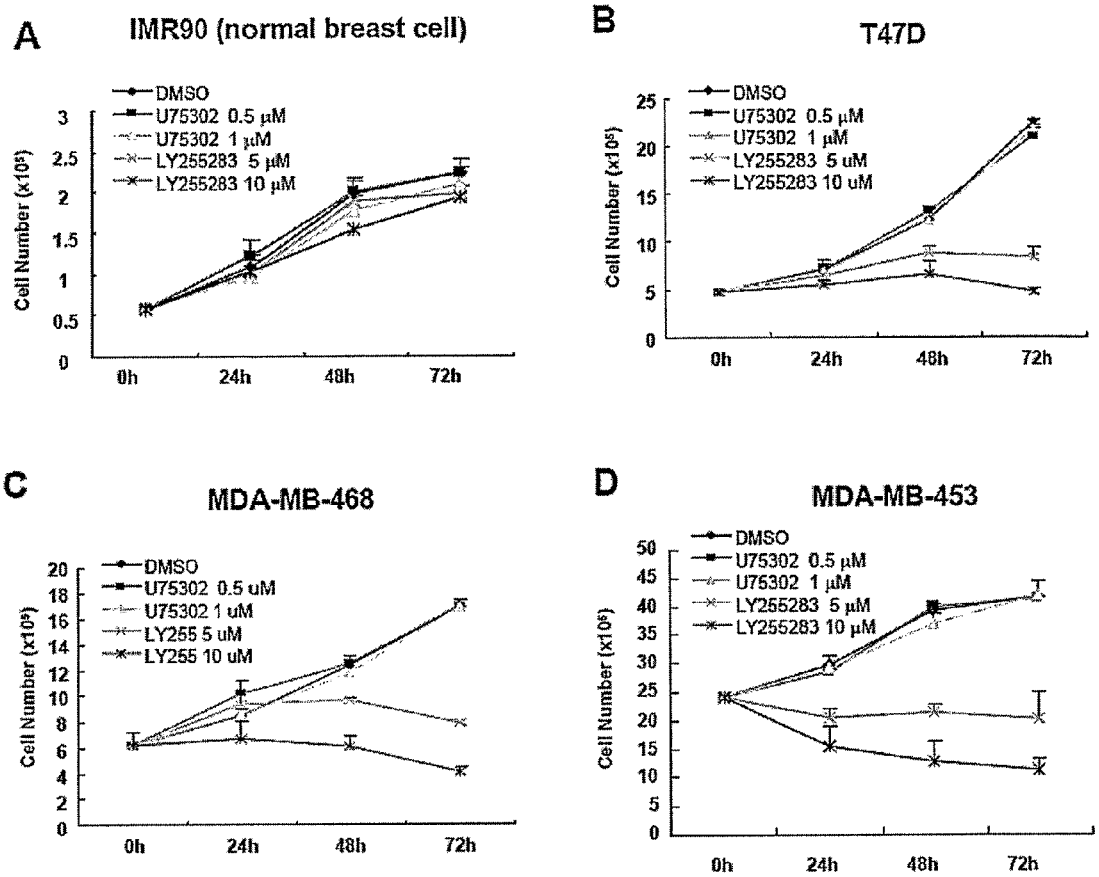
FIG. 1g shows the effect of BLT2 antagonist LY255283 on breast cancer cell viability. The BLT2 antagonist significantly reduced breast cancer cells viability.

BLT2 Antagonist Significantly Reduced Breast Cancer Cells Viability (1) Cell Growth Assay (A-D of FIG. 1g)

To investigate the effect of BLT2 antagonist, LY255283 and BLT1 antagonist, U75302 on growth of breast cancer, we used breast cancer cell line, T47D (ER+), MDA-MB-468 (ER−), MDA-MB-453 (ER−) and normal IMR-90 cells. Cells were treated with LY255283 and U75302 in a dose-dependent manner and analyzed for cell number using the trypan blue dye exclusion method. Cells were plated at a density of $0.5 \times 10^5$ or $5 \times 10^5$ cells/well on 12-well plate. After 24 h, cells were incubated in media containing 0.5% serum for 3 h. Then, cells were treated with U75302 (0.5, 1 μM), LY255283 (5, 10 μM) and incubated at 37° C. for indicated time (24, 48, and 72 h). To measure the growth of cell, the treated cells were then trypsinized at each time point, and counted by the trypan-blue exclusion method The treatment of LY255283 for blockade of BLT2 signaling significantly inhibits the growth of all of the breast cancer cell lines via a dose- and time-dependent manner. In addition, normal IMR-90 did not affect by LY255283. Contrast to LY255283, U75302 had no effect on growth of both breast cancer cells and normal cells. These results suggest that BLT2 signaling play a key role on growth of breast cancer. This indicates the possibility that BLT2 is a potential therapeutic target in breast cancer.

EXAMPLE 7

LY255283 Induces a Partial Apoptotic Cell Death in Breast Cancer Cells

To test involvement of BLT2 signaling on survival of breast cancer cells, the treated cell with BLT antagonist were analyzed for measure of apoptosis using DAPI staining and DNA fragmentation assay.

Figure 1H:
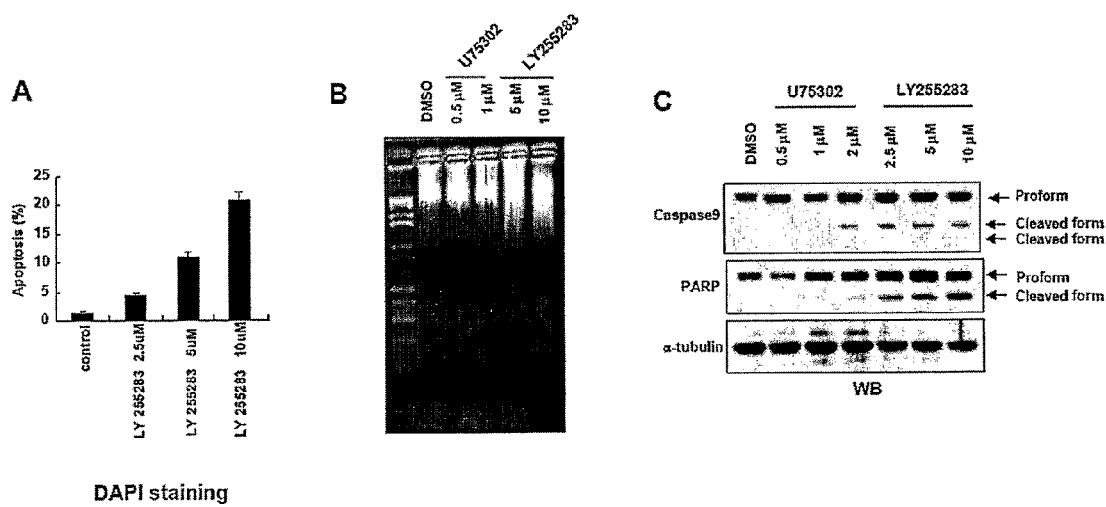
FIG. 1h shows the effect of BLT2 antagonist LY255283 on breast cancer cell apoptosis. The LY255283 induced a partial apoptotic cell death in breast cancer cells.

(1) DAPI Staining (A of FIG. 1h)

Cells were grown on sterile coverslips at a density of $7 \times 10^5$ cells/plate in 35-mm plate. After 24 h, cells incubated in media containing serum-free for 3 h. Then, cells were treated with U75302 (0.5, 1 μM), LY255283 (5, 10 μM) and incubated at 37° C. for 48 h. Then, cells were fixed with 70% cold-ethanol for 30 min at room temperature, and then washed once with PBS. DAPI (50 ng/ml) was added to the fixed cells, incubated for 20 min at room temperature, and washed with PBS. Cells were mounted and examined by fluorescence microscopy. Apoptotic cells were identified by the condensation and fragmentation of their nuclei. The percentage of apoptotic cells was calculated as the ratio of apoptotic cells to total cells counted. A minimum of 500 cells were counted for each treatment.

(2) DNA Fragmentation Assay (B of FIG. 1h)

Cells were plated a density of $2 \times 10^6$ cells/plate in 100-mm plate. After 24 h, cells incubated in media containing serum-free for 3 h. Then, cells were treated with U75302 (0.5, 1 μM), LY255283 (5, 10 M) and incubated at 37° C. for 48 h. Both attached and detached cells were collected and resuspended in a lysis buffer (20 mM Tris/HCl, pH 8.0, 0.1 mM EDTA, 1% SDS, and 0.5 mg/ml proteinase K) and then incubated at 50° C. for overnight. DNA was extracted with phenol/chloroform. DNA sample were electrophoresed on 1.8% agarose gel and visualized by ethidium bromide staining.

(3) Western Blotting (C of FIG. 1h)

Cells were plated a density of $2 \times 10^6$ cells/plate in 100-mm plate. After 24 h, cells incubated in media containing serum-free for 3 h. Then, cells were treated with U75302 (0.5, 1 μM), LY255283 (5, 10 M) and incubated at 37° C. for 48 h. Both attached and detached cells were collected and lysed with buffer (40 mM Tris-HCl pH 8.0, 120 mM NaCl, 0.1% Nonidet-P40, 100 mM phenylmethylsulfonyl fluoride, 1 mM Na orthovanadate, 2 ug/ml leupeptin, 2 ug/ml aprotinin). Proteins were separated by SDS-PAGE and transferred onto a nitrocellulose membrane. The membrane was blocked with 5% nonfat dry milk in Tris-buffered saline and then incubated with primary antibodies against caspase-9, PARP for 1 h at room temperature. Blots were developed with a peroxidase-conjugated secondary antibody and proteins were visualized by enhanced chemiluminescence (ECL) procedures (Amersham, USA) according to the manufacturer's recommendation Treatment of LY255283 (2, 5, 10 μM) induces apoptosis via a dose-dependent manner in MDA-MB-468 cells (A). Consistent with DAPI staining, DNA fragmentation analysis of LY255283-treated MDA-MB-468 cells showed a laddering pattern characteristic of apoptosis (B). However, U75302 (0.5, 1 μM) did not induce DNA fragmentation (B). Next, to test whether caspase are involved in LY255283-induced apoptosis, activation of caspase-9 and PARP cleavage was analyzed using Western blotting. LY255283 induces a dose-dependent activation of caspase-9 and cleavage of PARP(C). However, U75302 did not affect on caspase-9 activation and PARP cleavage (C). These results demonstrate that LY255283, BLT2 antagonist, induces apoptosis via caspase-dependent signaling in breast cancer cells.

EXAMPLE 8

Combined Therapy (LY255283 and Epirubicin) Induce a Synergistic Apoptosis in Breast Cancer MCF7

(1) Cell Culture and Agents

The MCF-10A cells were grown in DMEM/F-12 (50:50, v/v) medium supplemented with 5% (v/v) horse serum, 100 units/ml penicillin, 100 mg/ml streptomycin, 0.5 mg/ml hydrocortisone, 100 ng/ml cholera toxin, 10 mg/ml insulin, 10 ng/ml epidermal growth factor and 1% (w/v) L-glutamine at 37° C. under a humidified 95%/5% (v/v) mixture of air and $CO_2$. MCF-7 cells were grown in RPMI 1640 supplemented with 10% heat inactivated FBS, 100 units/ml penicillin, and 100 μg/ml streptomycin at 37° C. under a humidified 95%/5% (v/v) mixture of air and $CO_2$. BLT2 antagonist (LY255283) was purchased from BIOMOL (Plymouth Meeting, Pa.). Epirubicin was purchase from MP Biomedicals. Cells were cultured for 24 h. After serum-starved for 6 h, cells were treated with 10 μM LY255283, 100 ng/ml epirubicin, or combination treatment in which cells were preincubation with LY255283 for 30 min before epirubicin treatment. In MCF-7 human breast cancer cells, BLT2 mRNA level was highly induced by RT-PCR analysis. However, in MCF-10A human normal breast cells, no induced expression of BLT2 is detected. These results for expression of BLT2 mRNA in human breast cancer cell indicate that the BLT2 may play an important role in breast cancer.

Figure 1I:
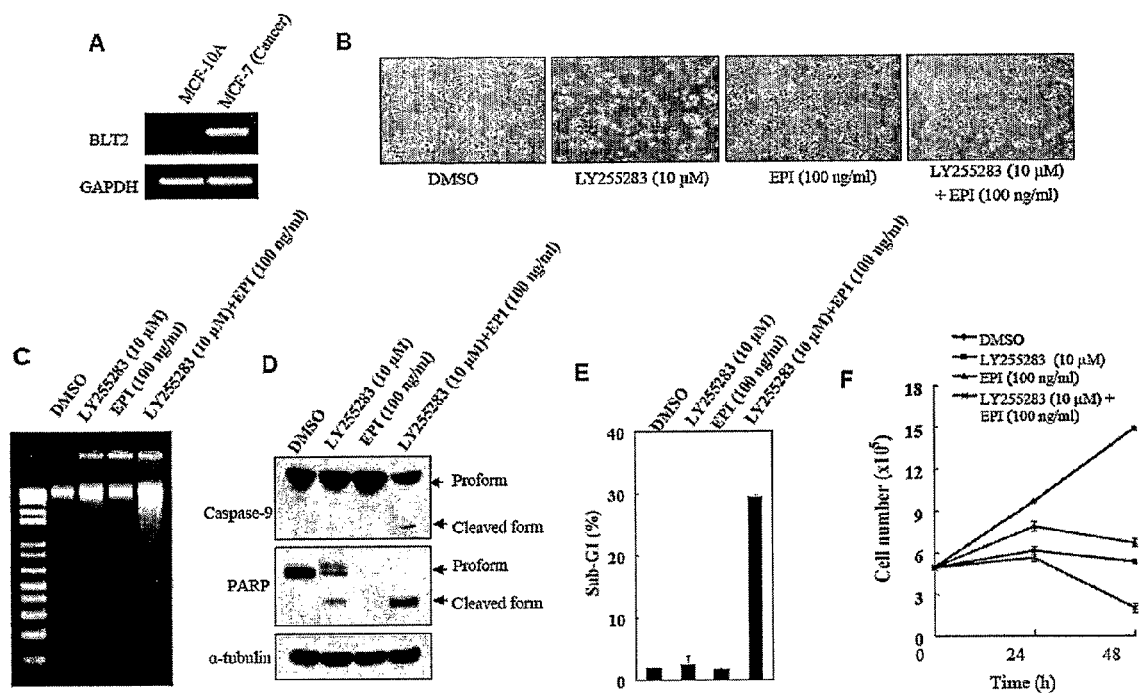
FIG. 1i shows the effect of combined treatment of BLT2 antagonist LY255283 with epirubicin on breast cancer cells. The combined therapy (LY255283 & epirubicin) induced a synergistic apoptosis in breast cancer MCF7.

(2) RT-PCR of BLT2 (A of FIG. 1i)

Total cellular RNA was extracted with Easy Blue™ (Intron, Korea). Thereafter, 1.25.mu.g of total RNA was reverse transcribed for 1 h at 42° C. and amplified by PCR with specific primers for human BLT2 (sense, 5'-AGCCTG-GAGACTCTGACCGCTTTCG-3'SEQ ID NO: 9; antisense, 5'-GACGTA GAGC ACCGGGTTGACGCTA-3', SEQ ID NO: 10). The PCR protocol for BLT2 involved 33 cycles of denaturation at 94° C. for 60 s, annealing at 68° C. for 40 s, an elongation at 72° C. for 45 s. Amplified PCR products were subjected to electrophoresis on 1.5% agarose gel, after which bands were visualized by ethidium bromide staining and visualized under UV illumination.

(3) Morphological Changes Using Light Microscopy (B of FIG. 1i)

Cells were seeded in 6 well-plate. After serum-starved for 6 h, cells were treated with 10 µM LY255283, 100 ng/ml epirubicin, or combination treatment in which cells were preincubation with LY255283 for 30 min before epirubicin treatment. Cells were cultured for 48 h. Cells were then viewed using light microscopy (×20). The morphology of cells was examined under light microscopy (×20). The treatment with the combination of LY255283 (10 µM) plus epirubicin (100 ng/ml) induced dramatic morphological changes in MCF-7 cells at 48h. Over time, the treated cells became rounded and exhibited membrane blebbing, chromatin condensation, and nuclear fragmentation and finally detached from the microplate. These morphological changes have been previously interpreted as reflecting apoptosis.

(4) DNA fragmentation assay (C of FIG. 1i)

After exposure to treatments, both attached and detached cells were harvested and suspended in lysis buffer (10 mM Tris-HCl, pH 8.0, 120 mM NaCl, 1 mM EDTA, and 1% SDS) containing proteinase K (100 µg/ml) on ice. Crude DNA samples were extracted twice with phenol/chloroform/isoamyl alcohol (25:24:1) and precipitated with absolute ethanol. The DNA pellet was resuspended in Tris-EDTA and 10 mg/ml RNase A. DNA samples were electrophoresed on 1.8% agarose gel and visualized by ethidium bromide staining. Epirubicin caused only tiny increase in cell death. However, when LY255283 (10 µM) is treated along with epirubicin (100 ng/ml) together, a sinergistic enhanced DNA fragmentation was observed.

(5) Western Blot Analysis (D of FIG. 1i)

Cellular protein was isolated with a protein extraction buffer containing 120 mM NaCl, 40 mM Tris-HCl (pH 8.0) and 0.1% NP-40. Equal amounts (100 µg/ml) of proteins were fractionated on 10% SDS-PAGE gels and transfered to polyvinylidene difluoride membranes. The membranes were then blocked for 1 hr with TBS containing 0.05% (v/v) Tween 20 plus 5% (w/v) nonfat dry milk and incubated with anti-PARP and casepase-9 primary antibodies, respectively. After washing with TBS containing 0.05% (v/v) Tween 20, the membranes were incubated with HRP-conjugated secondary antibody followed by enhanced chemiluminescent staining using the ECL system (Amersham Biosciences, UK). To assess if the cell death observed above represents apoptosis, a western blot analysis of apoptotic proteins was performed with epirubicin, LY355283, or a combination of the two drugs. When cells treated with two drugs, casepase-9 has become activated. PARP cleavage was detectable when cells treated with LY255283 alone (10 µM) but epirubicin alone (100 ng/ml). In contrast, the cleaved PARP band was much more noticeable with the combination treatment of two drugs. These results indicated that combination of LY255283 and epirubicin induces apoptosis through caspase-dependent pathway in MCF-7 cells.

(6) Cell Cycle Analysis (E of FIG. 1i)

Flow cytometric analysis was performed to detect and quantify apoptosis. Cells were fixed in PBS with 70% ethanol overnight. After centrifugation, the cells were washed with PBS and resuspended in a solution of PBS with RNase A (100 µg/ml) for 30 min at 37° C. Propidium iodide (50 µg/ml) was then added before FACS. Acquisition and analysis was performed by FACScan using Cell Quest Alias software (BD Bioscience). Cells with their DNA content less than that of $G_1$ phase cells (sub-$G_1$) were assumed to be apoptotic. Sub-G1 population is highly increased by the combined treatment of LY255283 (10 µM) with epirubicin (100 ng/ml) by FACS analysis.

(7) Cell Growth (F of FIG. 1i)

To determine the rate of cell growth, cells were seeded at approximately $2.5 \times 10^5$ cells/35-mm. The cell were treated with 10 µM LY255283 and 100 ng/ml epirubicin for 24 h and 48 h. At times indicated, plates were rinsed twice with PBS to remove dead cells and debris. Live cells on the plates were trypsinized and collected separately. Cells from each plate were counted four times using the Coulter cell counter. The average number of cells from plates was used for growth rate determination. Cell number is decreased significantly by the combined therapy of LY255283 (10 µM) with epirubicin (100 ng/ml).

EXAMPLE 9

Figure 2A:
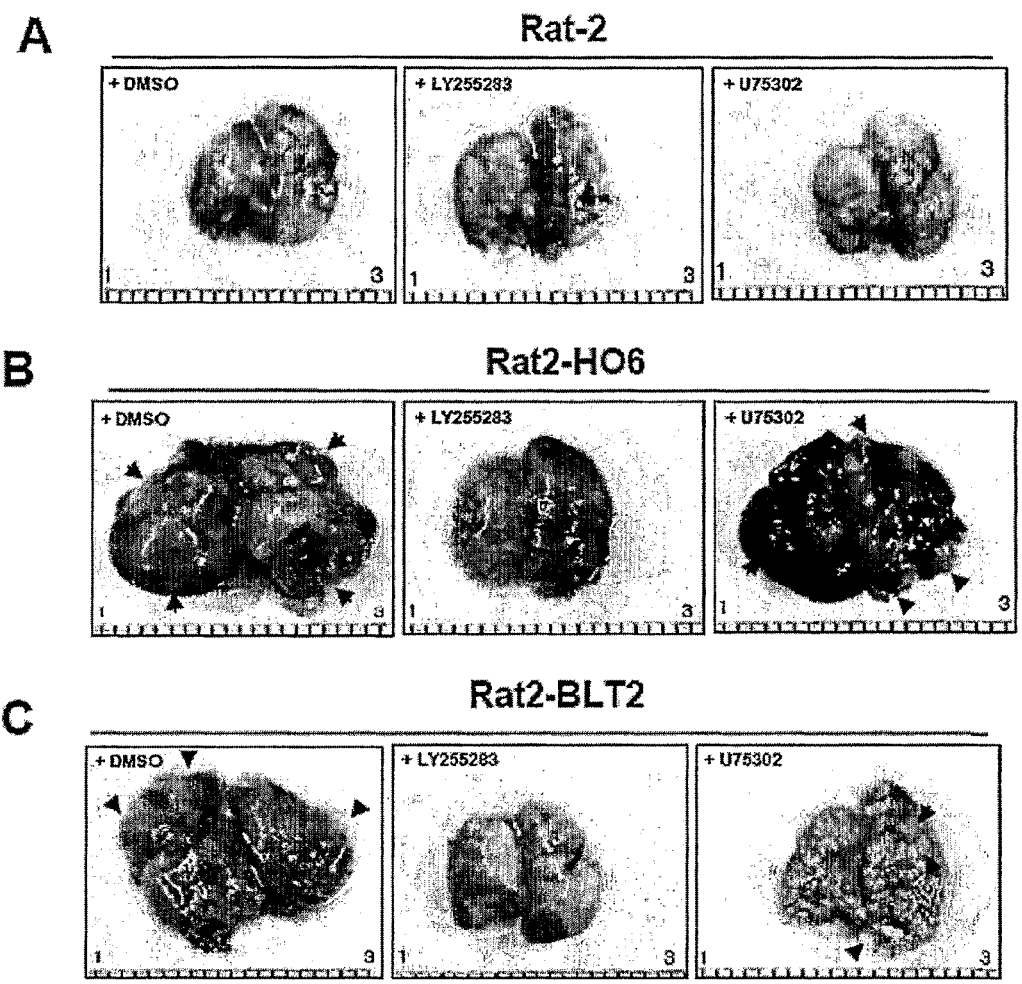
FIG. 2a shows the effect of BLT2 antagonist LY255283 on metastasis of cancer cells. The LY255283 suppressed metastasis of Ras-transformed cancer cells.

LY255283 Suppresses Metastasis of Ras-Transformed Cancer Cells (1) Experimental Metastasis Assay (A-C of FIG. 2a)

All experimental animals used in this study were treated according to guidelines approved by the Institutional Animal Care and Use Committee of Korea University. Female nude mice (Charles River, Wilmington, Mass.), four-weeks-old at the time of injection, were used in the experimental metastasis assay. Rat-2, Rat2-HO6, and Rat2-BLT2 cells ($5 \times 10^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing $LTB_4$, and injected within 1 hr in 0.1 ml into the lateral tail vein with a 26-gauge needle. For inhibitor experiments, U75302 and LY255283 (0.25 mg/kg for BLT1 antagonist and 2.5 mg/kg for BLT2 antagonist) was injected intraperitoneally 3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (7 weeks) (n=8, each group).

BLT2 antagonist LY255283 significantly reduced Ras-oncogene expressing transformed cell metastasis in nude mouse. In vivo lung metastasis driven by (B) H-$Ras^{V12}$ or (C) BLT2 is reduced by BLT2 inhibition (LY255283) based on the macroscopic and histologic appearance of lung. However, (A) the control Rat-2 cells injection causes no metastasis in lung. Unlike to LY255283, DMSO or U75302 cause no suppression on metastasis in response to H-Ras$^{V12}$ or BLT2. Mice were euthanized 21 days after cell injection, and the number of lung metastasis nodules and weight of lung was analyzed in each group. All experimental animals used in this study were treated according to guidelines approved by the Institutional Animal Care and Use Committee of Korea University. Female nude mice (Charles River, Wilmington, Mass.), four weeks old at the time of injection, were used in the experimental metastasis assay. Rat-2, Rat2-HO6, and Rat2-BLT2 cells (5×10$^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing LTB$_4$, and injected within 1 hr in 0.1 ml into the lateral tail vein with a 26-gauge needle. For inhibitor experiments, DMSO, U75302, or LY255283 (2.5 mg/kg for BLTs antagonist) was injected intraperitoneally 3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (for 7 weeks) (n=8, each group). The lungs were dissected and fixed in 4% formalin, processed, and embedded in paraffin. Sections (4 µm) were stained with hematoxylin and eosin, and examined and photographed using a BX51 microscope (Olympus, Tokyo, Japan) equipped with a DP71 digital camera (Olympus). Metastasis survival was analyzed in Kaplan-Meyer plots.

EXAMPLE 10

Figure 2B:
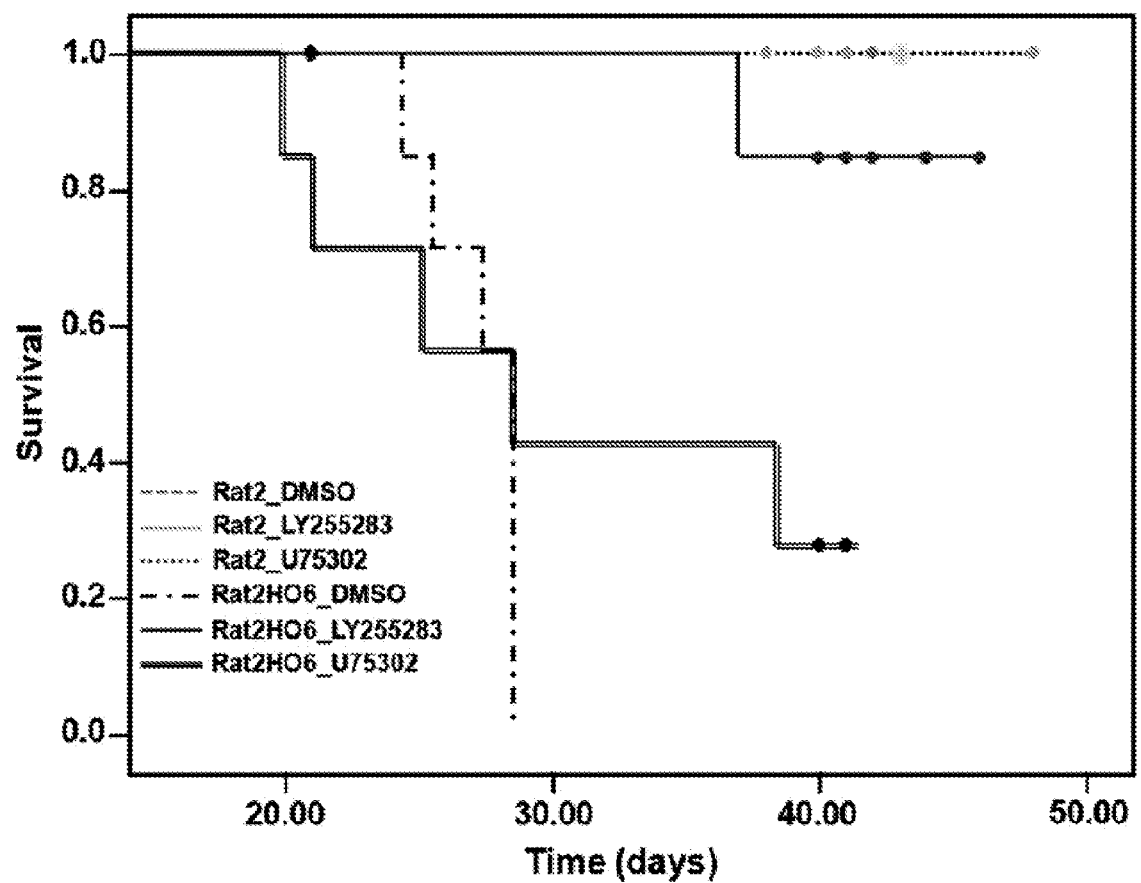
FIG. 2b shows the effect of BLT2 antagonist LY255283 on the survival of mouse injected with Ras-oncogene expressing transformed cells. The LY255283 extended the survival of mouse injected with Ras-cancer cells.

LY255283 Extends the Survival of Mouse Injected with Ras-Cancer Cells (1) Experimental Metastasis Assay and Metastasis Survival Analysis (FIG. 2b)

All experimental animals used in this study were treated according to guidelines approved by the Institutional Animal Care and Use Committee of Korea University. Female nude mice (Charles River, Wilmington, Mass.), four-weeks-old at the time of injection, were used in the experimental metastasis assay. Rat-2, Rat2-HO6, and Rat2-BLT2 cells (5×10$^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing LTB$_4$, and injected within 1 hr in 0.1 ml into the lateral tail vein with a 26-gauge needle. For inhibitor experiments, U75302 and LY255283 (0.25 mg/kg for BLT1 antagonist and 2.5 mg/kg for BLT2 antagonist) was injected intraperitoneally 3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (7 weeks) (n=8, each group). Metastasis survival was analyzed in Kaplan-Meyer plots.

BLT2 antagonist LY255283 extends the survival of mouse injected with Ras-oncogene expressing transformed cells. The mortality of mice injected with Rat2-HO6 cells is attenuated by inhibition of BLT2 signaling according to the Kaplan-Meier survival analysis.

EXAMPLE 11

BLT2 Plays a Critical Role in Angiogenesis (1) Preparation and Identification of BLT2 Transgenic (TG) Mice The complete rat BLT2 gene was subcloned from pcDNA3-HA-rBLT2 and inserted into the pCAGGS-B2 vector downstream of the chicken β-actin promoter. The digested and purified construct was injected into fertilized eggs and those eggs were subsequently implanted in foster females. Potential transgenic founder mice were screened by PCR with 2 different primer sets using genomic DNA extracted from the tails of 3-week-old mice to detect transgene integration. Briefly, the mouse tail biopsy was put into 200 µl TES buffer (50 mM Tris-Cl, pH 8.0, 50 mM EDTA, 0.5% SDS). Proteinase K (final concentration: 200 µ/ml) was added and it was incubated overnight at 55° C. Mouse genomic DNA was obtained after phenol extraction and ethanol precipitation. The primers for screening the BLT2 transgenic mice were as follows: forward, 5'-GCGCAGGGACTTCCTTTGTC-3', SEQ ID NO: 13 and 5'-GCTCTAGAGCCTCTGCTAACC-3', SEQ ID NO: 14; reverse, 5'-CCGATGGGTGGCACAAT-TGAC-3', SEQ ID NO: 15. The PCR protocol for BLT2 involved 35 cycles of denaturation at 96° C. for 60 s, annealing at 52° C. for 30 s, and elongation at 72° C. for 120 s, followed by an extension at 72° C. for 10 min. The amplified PCR products (924 by and 677 bp, respectively) were subjected to electrophoresis on a 1.0% agarose gel, after which the bands were visualized by ethidium bromide staining. The positive founder obtained was bred with female mice of the same strain (FVB). Potential positive litters (F1) were screened by PCR as described above. To verify BLT2 overexpression, total RNA was isolated from 6-wk-old BLT2 transgenic mice and age-matched control mice using Easy Blue™. Thereafter, 1 µg of total RNA was reverse transcribed for 60 minutes at 42° C. and amplified by PCR with primers for mouse BLT2, (forward, 5'-CAGCATGTACGC-CAGCGTGC-3', SEQ ID NO: 16; reverse, 5'-CGATG-GCGCTCACCAGACC-3', SEQ ID NO: 17). The PCR protocol involved 28 cycles of denaturation at 95° C. for 30 s, annealing at 69° C. for 30 s, and elongation at 72° C. for 45 s, followed by an extension at 72° C. for 10 min. The PCR products were separated by electrophoresis on 1.5% agarose gels and stained with ethidium bromide.

(2) In Vivo Matrigel Plug Assay

FVB wild-type mice or BLT2 TG mice (female, 8-10 wk old) were subcutaneously injected with 400 µl of growth factor-reduced Matrigel from BD Biosciences containing heparin (20 units) and the agents to be tested. After 7 d, the mice were killed, and the solidified Matrigel was excised, fixed in 10% formalin, embedded in paraffin, cut into 5-µm sections and stained with anti-vWF antibody according to the manufacturer's instructions in the Blood Vessel Staining Kit (Chemicon). Each stained Matrigel section was photographed using a BX51 microscope equipped with a DP71 digital camera (Olympus), and the area of vWF-positive blood vessels was calculated using Image J software.

Figure 3A:
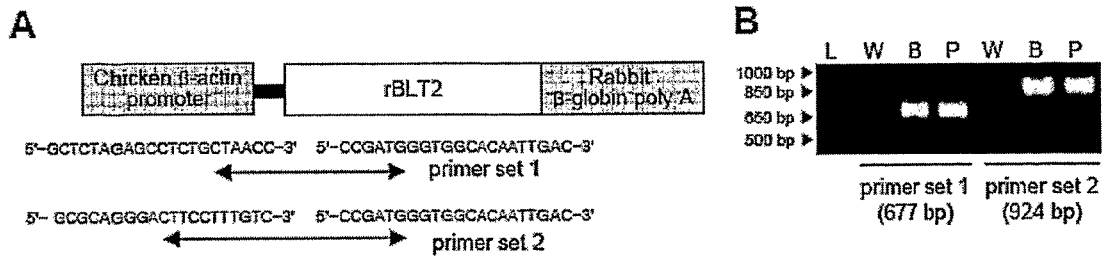
FIG. 3a shows the effect of BLT2 stimulation on tumor angiogenesis BLT2 stimulation induces tumor angiogenesis in vivo. The primers for screening BLT2 expression were as follows: forward, 5'-GCGCAGGGACTTCCTTTGTC-3', SEQ ID NO: 13 and 5'-GCTCTAGAGCCTCTGCTAACC-3', SEQ ID NO: 14; reverse, 5'-CCGATGGGTGGCACAAT-TGAC-3', SEQ ID NO: 15.
Figure 3A:
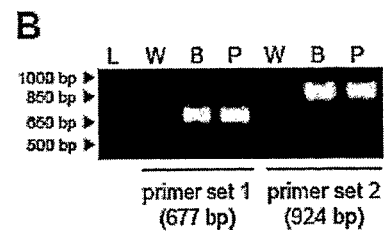
Figure 3A:
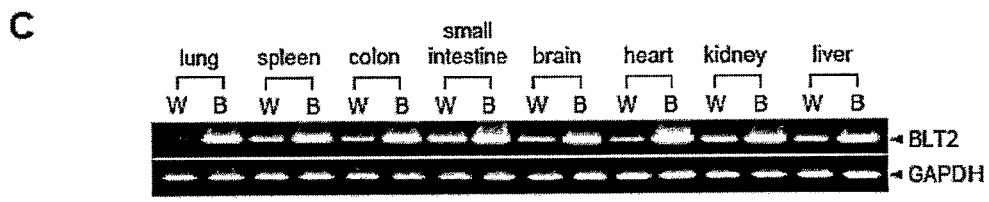
Figure 3A:
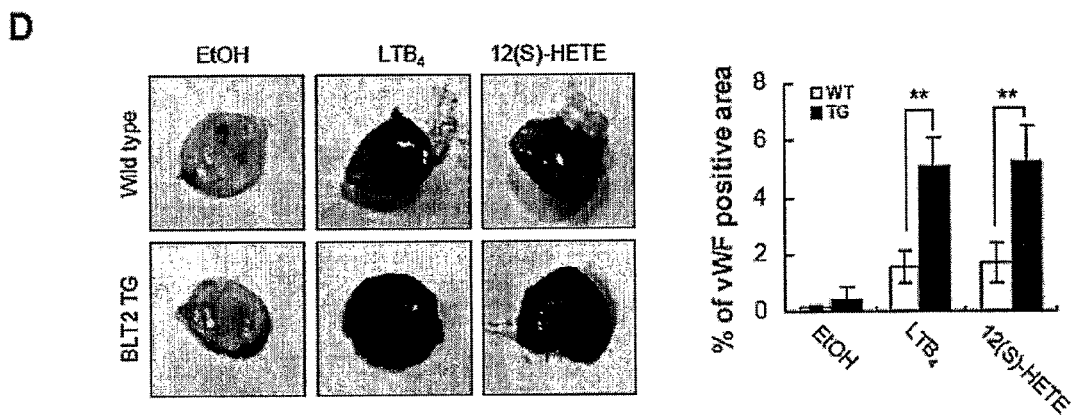

(3) BLT2 Play a Critical Role in Angiogenesis (A-D of FIG. 3a)

(A) Schematic of the DNA construct used to generate BLT2 TG mice. The two sets of forward and reverse primers are indicated. (B) Identification of founders using PCR. Genomic DNA from a tail biopsy was amplified using the two indicated primer sets. The 677-bp PCR product formed with primer set 1 and the 924-bp product formed with primer set 2 are shown. The DNA construct used to generate BLT2 TG mice was used as a template for the positive control. L: DNA ladder, W: wild-type mice, B: BLT2 TG mice, P: positive control. (C) Overexpression of BLT2 mRNA in various organs of BLT2 TG mice. Total RNA was isolated, reverse transcribed and amplified using specific primers for BLT2 and GAPDH. W: wild type mice, B: BLT2 TG mice. (D) FVB WT and BLT2 TG mice were subcutaneously injected with growth factor-reduced Matrigel containing heparin (20 units) and EtOH, LTB$_4$ (1 µg) or 12(S)-HETE (0.5 µg). In vivo vessel formation was assayed as described above. Data are expressed as mean fold increases over control.

EXAMPLE 12

BLT2 Antagonist, LY255283 Suppresses VEGF-Induced Angiogenesis (1) Tube Formation Assay 300 µl of growth factor-reduced Matrigel (BD Biosciences, San Diego, Calif.) was added to each 24-well plate and polymerized for 12 h at 37° C. HUVECs that had been incubated in M199 medium containing 5% FBS for 4 h were trypsinized and suspended in M199 medium containing 1% FBS. If called for, the cells were pre-treated with inhibitors or antagonists for 30 min before being seeded onto the Matrigel layer to a density of 5×10$^4$ cells/well. Cells were then stimulated with LTB$_4$, 12(S)-HETE or VEGF. After 12 h, five randomly selected areas were photographed using a CKX41 microscope equipped with a DP71 digital camera, and tube lengths were measured and quantified using Image J software, the image processing program developed at the U.S. National Institutes of Health (NIH).

(2) Transmigration Assay

Transmigration assays were performed using Transwell chambers (Corning Costar, Cambridge, Mass.) with 6.5-mm diameter polycarbonate filters (8-µm pore size). Confluent HUVECs were incubated for 4 h in M199 medium containing 5% FBS. The lower surfaces of the filters were coated with 10 µl of 1% gelatin for 1 h at 37° C. Cells were trypsinized and suspended in M199 medium containing 1% FBS before being loaded into the upper chambers to a final concentration of 1×10$^5$ cells/well. The cells were then allowed to migrate to the lower side of the chambers, which contained LTB$_4$, 12(S)-HETE or VEGF. If called for, inhibitors or antagonists were applied to the cells in suspension for 30 min before seeding. After incubation for 3 h at 37° C. in 5% CO$_2$, the filters were disassembled, and the upper surface of each filter was scraped free of cells by wiping with a cotton swab. Cells that had migrated to the underside of the filter were fixed for 1 min in methanol, stained for 1 min in hematoxylin and finally stained for 30 s in eosin. Cell migration was quantified by counting the cells on the lower side of the filter after they were photographed using a CKX41 microscope equipped with a DP71 digital camera. Five fields were counted in each assay.

Figure 3B:
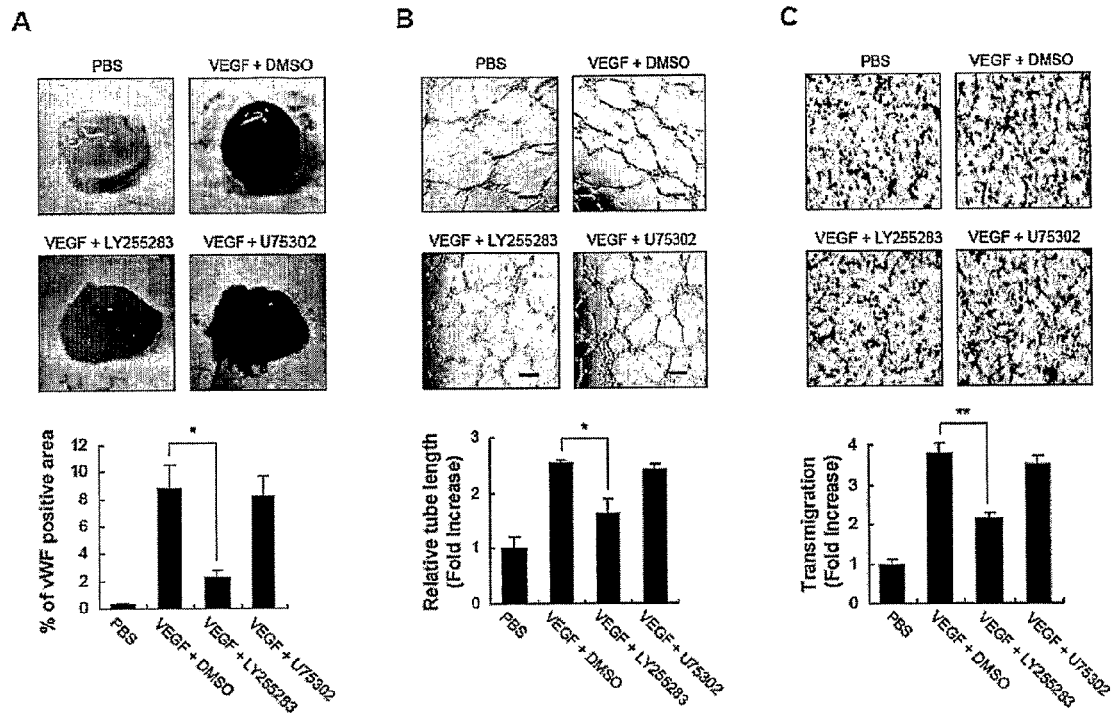
FIG. 3b shows the effect of BLT2 antagonist 255283 on VEGF-induced angiogenesis. The BLT2 antagonist LY255283 suppressed VEGF-induced angiogenesis.

(3) BLT2 Antagonist 255283 Suppresses VEGF-Induced Angiogenesis (A-C of FIG. 3b)

(A) FVB mice were injected subcutaneously with 400 µl of growth factor-reduced matrigel containing heparin (20 units) and PBS, VEGF (100 ng), VEGF+LY255283 (10 µg), VEGF+U75302 (1 µg) or VEGF+DMSO. After 7 d, the mice were killed and the solidified matrigel was excised, fixed in 10% formalin, embedded in paraffin, cut into 5 µm sections and stained with anti-von Willebrand factor (vWF) antibody according to the manufacturer's instructions for the Blood Vessel Staining Kit (Chemicon). Each stained matrigel was photographed using a BX51 microscope (Olympus) equipped with a DP71 digital camera and the area of vWF-positive blood vessels was calculated using Image J software. The photographs show representative results that were obtained with each treatment. (B) HUVECs were incubated in M199 medium containing 5% FBS for 4 h and LY255283 and U75302 were added for 30 min to the cells in suspension in M199 medium containing 1% FBS. The cells were plated on growth factor-reduced matrigel-coated 24-well plates and stimulated with VEGF. After 12 h, five randomly selected areas were photographed and tube lengths were measured using Image J software. Bars represent 100 µm. (C) HUVECs were incubated in M199 medium containing 5% FBS for 4 h and LY255283 and U75302 were added for 30 min to cells suspended in M199 medium containing 1% FBS. The cells were loaded into the upper well and VEGF was present in the lower well. After 3 h, cells that had migrated to the lower side were stained and counted.

EXAMPLE 13

Figure 4A:
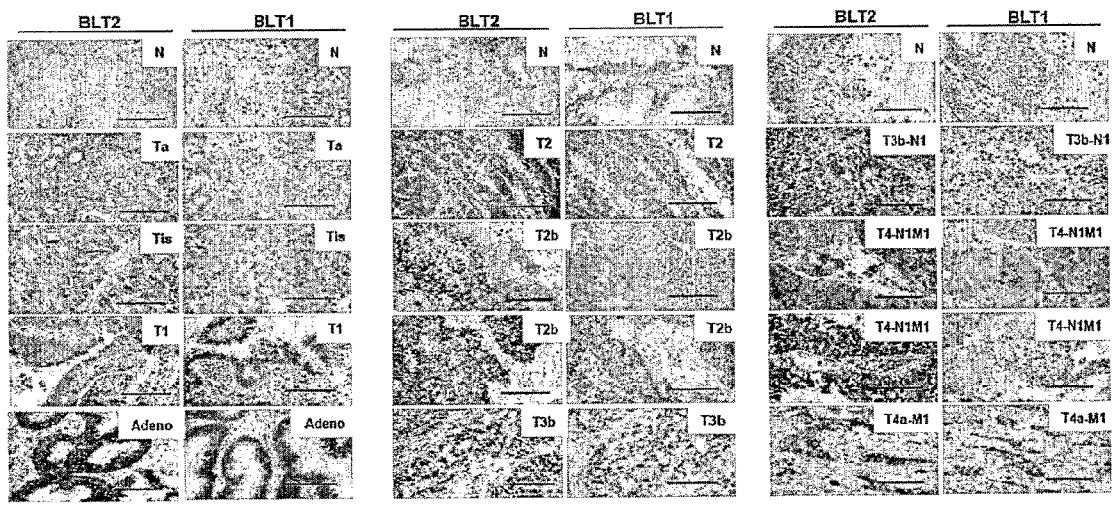
FIG. 4a shows enhanced overexpression of BLT2 in bladder cancer clinical specimens. The expression of BLT2 was Induced in bladder tumor tissue sample: 85 patients.

Immunohistochemical Staining, Histologic Scoring, and Analysis (FIG. 4a)

Various human tumors and corresponding normal tissues/human bladder tumor tissue samples were purchased from Petagen Inc, (Korea). For antigen retrieval, formalin-fixed, paraffin-embedded sections were placed in proteinase K (Biogenex, USA) for 10 min before application of the rabbit polyclonal antibody to BLT1/2 (dilution 1:250) or MMP-9 (dilution 1:250, Sigma-Aldrich, Inc., Saint Louis, Mo.). After incubation with the primary antibody and with the biotinylated secondary antibody, streptavidin-coupled alkaline phosphatase was applied. Fast Red Violet (for BLT1/2 stain; Chemicon, Temecula, Calif., APR150) or Diaminobenzidine (for MMP-9 stain; Chemicon, Temecula, Calif., DAB150) was used as the chromogen. Sections were then counterstained with hematoxylin. Immunoreactivity was independently evaluated by two blinded observers. Cytoplasmic staining was graded for intensity (0-negative, 1-weak, 2-moderate, and 3-strong) and percentage of positive cells [0, 1 (1-24%), 2 (25-49%), 3 (50-74%), and 4(75-100%)] and discrepancies were resolved by consensus. The grades were then multiplied to determine an H-score (Camp et al., 1999; Ishibashi et al., 2003. The H-scores for tumors with multiple cores were averaged. Protein expression was then defined as low (H-score<130) or high (H-score>130). Chi-square analysis was used to analyze the relationship between BLT2 and MMP-9 expression.

TABLE 1

TMN stage and leukotriene B$_4$ receptors, BLT1 and BLT2, expression levels in bladder tumor tissue sample for 85 patients

| TMN stage (total no.) | BLT2 groups | | | BLT1 groups | | |
|---|---|---|---|---|---|---|
| | 1 | 2 | 3 | 1 | 2 | 3 |
| Stage 0 (18)   | 4 (22.2%)  | 9 (50%)    | 5 (27.8%)   | 11 (61.1%) | 7 (38.9%) | 0 (0%) |
| Stage I (28)   | 6 (21.4%)  | 11 (39.3%) | 11 (39.3%)  | 20 (71.4%) | 8 (28.6%) | 0 (0%) |
| Stage II (24)  | 0 (0%)     | 10 (41.7%) | 10 (41.7%)  | 12 (50%)   | 8 (33.3%) | 0 (0%) |
| Stage III (13) | 2 (15.4%)  | 5 (38.5%)  | 6 (46.2%)*  | 13 (100%)  | 0 (0%)    | 0 (0%) |
| Stage IV (6)   | 0 (0%)     | 0 (0%)     | 6 (100%)*   | 6 (100%)   | 0 (0%)    | 0 (0%) |

For consistency with our rating system, BLT1/BLT2 scores were translated a follows "0" and "1+"="1", "2+"="2", "3+"="3".

Expression Patterns in all samples are summarized here. The Person chi-square was used for comparisons with normal bladder (p<0.001).

The 85 specimens of bladder tumor were stained anti-BLT1 and anti-BLT2 antibody as shown below FIG. 4a shows enhanced expression of BLT2 in bladder tumor tissue of patients. (Top) To evaluate expression of BLT2 in various tumors and corresponding neoplastic tissues, IHC was carried out using anti-rabbit BLT2 antibody. Various human tumors corresponding normal tissues/human bladder tumor tissue samples were purchased from Petagen Inc. (Korea). Formalin-fixed, paraffin-embedded sections were placed in protenase K (Biogenex, USA) in order to antigen retrieval for 10 min before application of the rabbit polyclonal antibody to BLT1/2 (dilution 1:250). After incubation with the primary antibody, and addition of the biotinylated secondary antibody, streptavidin-coupled alkaline phosphatase was applied. Fast Red Violet (for BLT1/2 stain; Chemicon, Temecula, Calif., APR150) was used as the chromogen. Sections were then counterstained with hematoxylin. The results shown are representative of three independent experiments with similar results. BLT2 expression (red) shows strong cytoplasmic/plasmic membranous staining in various human tumors. Hematoxylin was used for counterstaining (blue). Bar, 100 μm. To examine whether BLTs expression is associated with the pathological potential of tumor, IHC was performed and investigated using scoring analysis. The results shown are representative of three independent experiments with similar results. N, normal bladder tissue; Ta/Tis, tumor without invasion; T1, tumors that had invaded the superficial muscle; T2/T2b, tumors with deep muscle invasion; T3b/T3b-N1/T4-N1M1/T4a-M1, tumors that had invaded the perivesical fat or metastasized the lymphatic organs or other adjacent organs (T3b/T3b-N1/T4-N1M1/T4a-M1 are considered as invasive tumors (T3/T4)). Ta/T is, Stage 0; T1, Stage I; T2/T2b, Stage II; T3, Stage III; T3b-N1/T4-N1M1/T4a-M1, Stage 1V (according to TNM classifications). Bar, 100 μm. (Bottom) Immunoreactivity was evaluated independently blindly by two observers. Cytoplasmic staining was graded for intensity (0-negative, 1-weak, 2-moderated, and 3-strong) and percentage of positive cells (0, 1 (1-24%), 2(25-49%), 3(50-74%), and 4(75-100%) with discrepancies resolved by consensus and the grades were multiplied to determine an H-score (Camp et al., 1999; Ishibashi et al., 2003. The H-scores for tumors with multiple cores were averaged. Protein expression was then defined as low (H-score<130), or high (H-score>130).

EXAMPLE 14

Figures 4B, 4C:
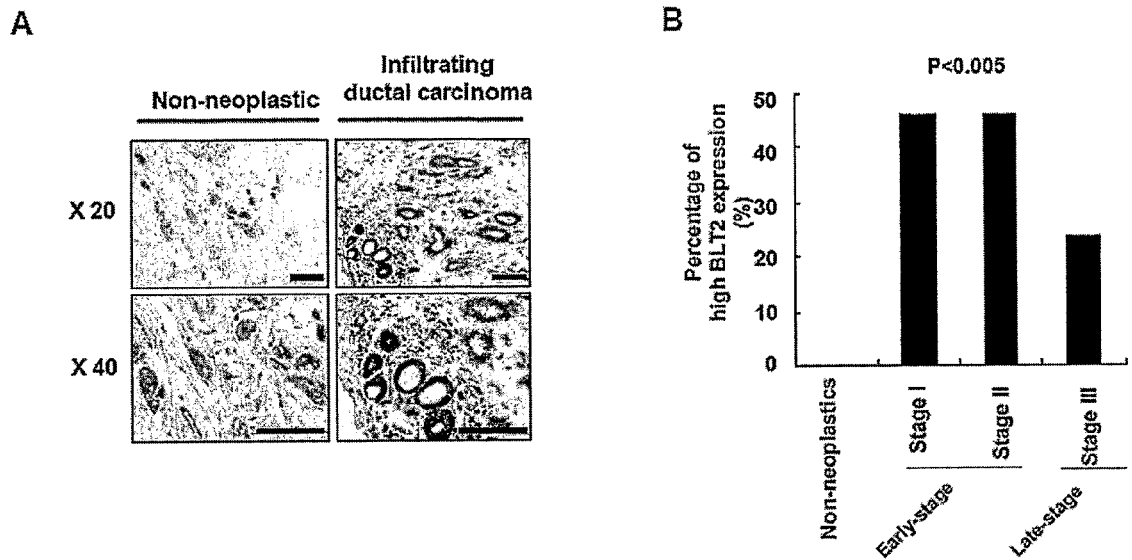
FIG. 4b shows enhanced overexpression of BLT2 in breast cancer clinical specimens. The induction of BLT2 was observed in human breast cancer.
FIG. 4c shows enhanced overexpression of BLT2 in breast cancer clinical specimens. The induction of BLT2 was observed in human breast cancer.

Induction of BLT2 in Human Breast Cancer (1) In Situ Hybridization for BLT2 (A of FIG. 4b)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various breast cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. Then, they photographed using a BX51 microscope (Olympus, Tokyo, Japan) equipped with DP71 digital camera (Olympus).

(2) In Situ Hybridization for BLT2 (B of FIG. 4b)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. To examine whether BLTs expression is associated with the pathological potential of tumor, IHC was performed and investigated using Chi-square test. FIG. 4b shows enhanced expression of BLT2 in breast cancer patients.
(3) In Situ Hybridization for BLT2 (FIG. 4c)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various breast cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. To examine whether BLTs expression is associated with the pathological potential of tumor, IHC was performed and investigated using Chi-square test.

FIG. 4c shows enhanced expression of BLT2 in breast cancer patients. Immunoreactivity was evaluated independently blindly by two observers. Cytoplasmic staining was graded for intensity (0-negative, 1-weak, 2-moderated, and 3-strong) and percentage of positive cells (0, 1 (1-24%), 2(25-49%), 3(50-74%), and 4(75-100%) with discrepancies resolved by consensus and the grades were multiplied to determine an H-score (Camp et al., 1999; Ishibashi et al., 2003. The H-scores for tumors with multiple cores were averaged. Protein expression was then defined as low (H-score<130), or high (H-score>130).

EXAMPLE 15

Figure 4D:
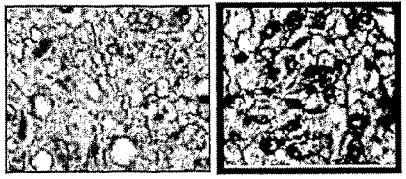
FIG. 4d shows enhanced overexpression of BLT2 in liver, brain, breast, skin, and thyroid cancer clinical specimens. The induced expression of BLT2 was observed in liver, brain, breast, skin, and thyroid tumor tissue.
Figure 4D:
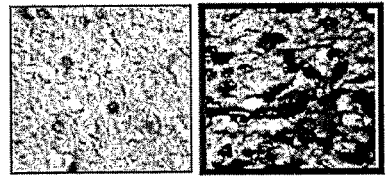
Figure 4D:
Figure 4D:
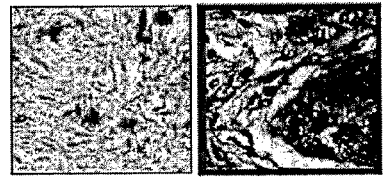
Figure 4D:
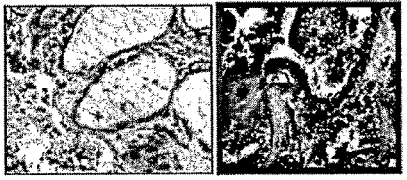
Figure 4D:

Induced Expression of BLT2 in Liver, Breast, Skin, and Thyroid Tumor Tissue (1) In Situ Hybridization for BLT2 (FIG. 4d)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various cancer tissue samples plus matching normal tissue arrays from Petagen Inc. (Korea) were deparaffinized with xylene, after which in situ hybridization was carried out using an in situ hybridization detection kit according to manufacturer's protocol (Inno-Genex, San Ramon, Calif., USA). Briefly, deparaffinized tissues were treated with Proteinase K and post-fixed with 1% formaldehyde in RNase-free PBS. After hybridizing the DIG-labeled probes for 16 h at 37 C, they were reacted with anti-DIG antibodies, and aminoethyl carbazole (AEC) reagent was used for color development. Mayer's hematoxylin served as the counter staining. Then, they photographed using a BX51 microscope (Olympus, Tokyo, Japan) equipped with DP71 digital camera (Olympus). FIG. 4d shows enhanced expression of BLT2 in liver, brain, breast, skin, and thyroid tumor tissue of patients.

EXAMPLE 16

Figure 5A:
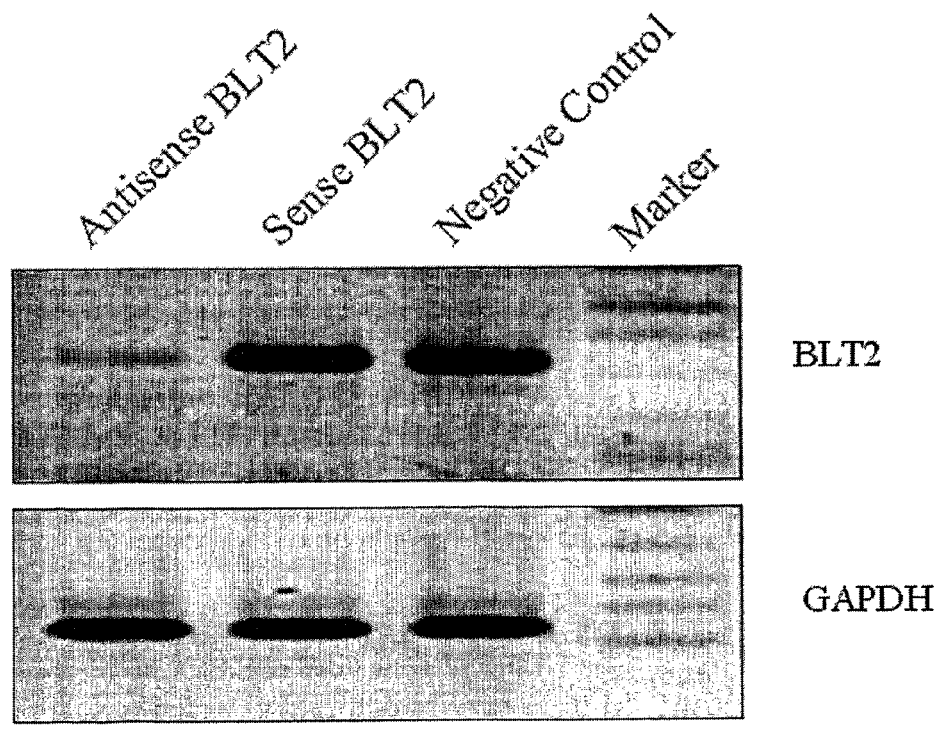
FIG. 5a shows the suppression effect of BLT2 antisense oligonucleotide on BLT2 expression level by RT-PCR.
Figure 5B:
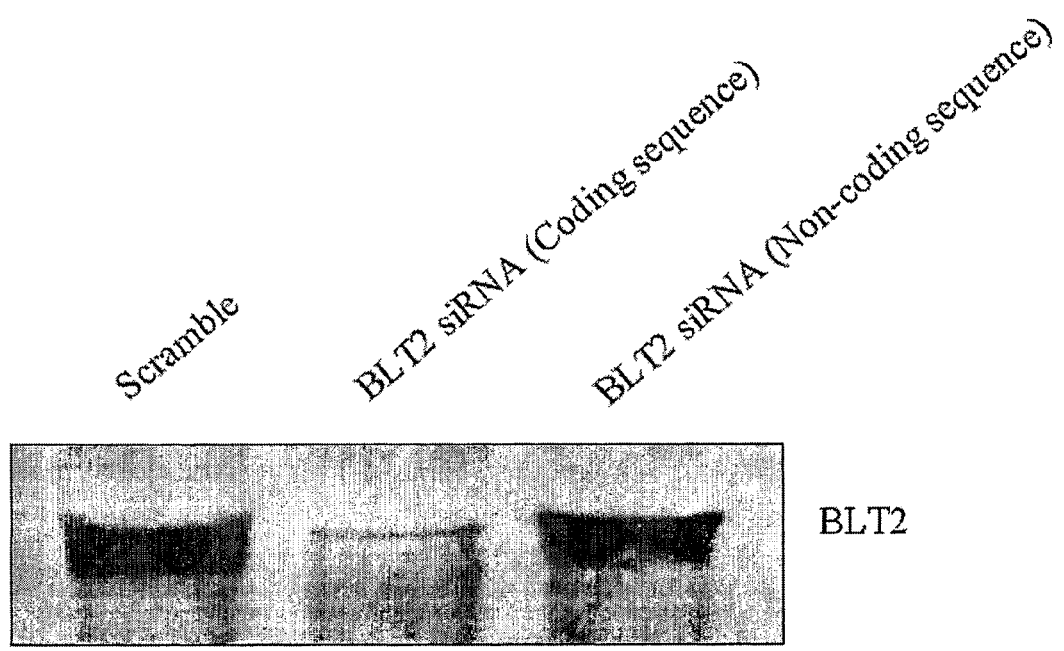
FIG. 5b shows the suppression effect of BLT2 siRNA on BLT2 expression level by Northern blot.

BLT2 Antisense Oligonucleotide Suppression Effect on BLT2 Expression (FIG. 5a)

Suppressed BLT2 expression level was determined by RT-PCR. Rat2-BLT2 stable cells were plated at a density of $5 \times 10^4$ cells/plate on 6 well plates. After 24 h, cells were transiently transfected with BLT2 specific antisense and sense oligonucleotide plasmid with Lipofectamin reagent and then incubated in fresh DMEM supplemented with 10% FBS for an additional 24 h. After additional incubation, the transfected cells were harvested for BLT2 transcripts analysis. Total RNA was reverse-transcribed and PCR amplify were performed with BLT2 forward primer: 5' tctcatcgggcat-cacaggt 3' and reverse primer: 5' ccaagctccacaccacgaag 3'. Non-transfected Rat2-BLT2 stable cells cDNA was used the negative control and GAPDH was shown as internal control. The result showed that the level of BLT2 mRNA was reduced by the antisense oligonucleotide, however the level of BLT2 mRNA was not affected by the sense oligonucleotide.

EXAMPLE 17

BLT2 siRNA Suppression Effect on BLT2 Expression

BLT2 siRNA expression effect on BLT2 expression was addressed by Northern blotting. CHO-BLT2 stable cells were plated at a density of $1 \times 10^5$ cells/plate on 60-mm dish. After 24 h, cells were transiently transfected with BLT2 specific siRNA, targeting for 1705-1724 by in NM_019839; 5' GAAGGATGTCGGTCTGCTA 3' (SEQ ID NO: 18), with oligofectamin reagent and then incubated in fresh RPMI 1640 supplemented with 10% FBS for an additional 24 h. after additional incubation, total RNA was performed Northern blot with [$^{32}$P]-dCTP labeled BLT2 probe. Scramble RNA and non-coding sequence BLT2 siRNA were used the negative control. A 110 by PCR fragment was amplified with pcDNA3.1-BLT2 clone using the following two primers, forward primer: 5'cttctcatcgggcatcacag 3' (SEQ ID NO: 19) and reverse primer: 5' atccttctgggcctacaggt 3'(SEQ ID NO: 20). This probe was located mainly in the BLT2 coding region. Total RNA was extracted with TRIzol reagent and then loaded the ten microgram total RNA for 2 h in MOPS containing agarose gel. After this step, the total RNA was transferred the Hybond N.sup.+membrane for overnight with 20×SSC buffer. The membrane was hybridized with [$^{32}$P]-dCTP labeled BLT2 probe in the hybridization buffer for 18 h at 68° C. And then, washed in 0.1×SSC (0.1% SDS) for 1 h at 68° C. and subjected to autoradiography. The result showed that the level of BLT2 mRNA was reduced by the BLT2 siRNA (coding sequence), however the level of BLT2 mRNA was not affected by the BLT2 siRNA (non-coding sequence).

As disclosed above, this invention is to make use of BLT2 inhibitors for (1) inducing apoptosis of cancer cells, (2) suppressing metastatic potential of cancer cells, (3) blocking angiogenesis of cancer cells. Also, this invention include (4) a novel strategy for screeing BLT2 signaling inhibitors by measuring the cell growth of Rat2-BLT2 stable cells. Lastly, this invention includes (5) the novel observation of BLT2 overexpression in various human cancers, which is a critical phenomena in tumorigenesis. Thus, this invention claims any use of strategy targeting against BLT2 verexpression or overactivation as a tool for developing therapeutic composition against human cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

[References]

Samuelsson, B.; Dahlen, S. E.; Lindgren, J. A.; Rouzer, C. A.; Serhan, C. N. Leukotrienes and lipoxins: structures, biosynthesis, and biological effects. *Science* 237:1171-1176; 1987.

Yokomizo, T.; Kato, K.; Terawaki, K.; Izumi, T.; Shimizu, T. A Second Leukotriene $B_4$ Receptor, BLT2: A New Therapeutic Target in Inflammation and Immunological Disorders. *J. Exp. Med.* 192:421-432; 2000.

Choi J A, Kim E Y, Song H W, Kim C M, and Kim J H. "ROS are generated through a BLT2-linked cascade in Ras-transformed cells" (2008) *Free Radical Biol & Med*, 44, 624-634.

Woo, C. H.; You, H. J.; Cho, S. H.; Eom, Y. W.; Chun, J. S.; Yoo, Y. J.; Kim, J. H. Leukotriene B(4) stimulates Rac-ERK cascade to generate reactive oxygen species that mediates chemotaxis. *J. Biol. Chem.* 277:8572-8578; 2002.

Yokomizo, T.; Izumi, T.; Chang, K.; Takuwa, Y.; Shimizu, T. A. G-protein-coupled receptor for leukotriene $B_4$ that mediates chemotaxis. *Nature* 387:620-624; 1997.

Chen, X. S.; Sheller, J. R.; Johnson, E. N.; Funk, C. D. Role of leukotrienes revealed by targeted disruption of the 5-lipoxygenase gene. *Nature* 372:179-182; 1994.

Griffiths, R. J.; Pettipher, E. R.; Koch, K.; Farrell, C. A.; Breslow, R.; Conklyn, M. J.; Smith, M. A.; Hackman, B. C.; Wimberly, D. J.; Milici, A. J. Leukotriene $B_4$ plays a critical role in the progression of collagen-induced arthritis. *Proc. Natl. Acad. Sci. USA* 92:517-521; 1995.

Turner, C. R.; Breslow, R.; Conklyn, M. J.; Andresen, C. J.; Patterson, D. K.; Lopez-Anaya, A.; Owens, B.; Lee, P.; Watson, J. W.; Showell, H. J. In vitro and in vivo effects of leukotriene $B_4$ antagonism in a primate model of asthma. *J. Clin. Invest.* 97:381-387; 1996.

Kamohara, M.; Takasaki, J.; Matsumoto, M.; Saito, T.; Ohishi, Y.; Ishii, H. M.; Furuichi, K. Molecular cloning and characterization of another leukotriene $B_4$ receptor. *J. Biol. Chem.* 275:27000-27004; 2000.

Blaine, S. A.; Wick, M.; Dessev, C.; Nemenoff, R. A. Induction of $cPLA_2$ in lung epithelial cells and non-small cell lung cancer is mediated by Sp1 and c-Jun. *J. Biol. Chem.* 276:42737-42743; 2001.

Heasley, L. E.; Thaler, S.; Nicks, M.; Price, B.; Skorecki, K.; Nemenoff, R. A. Induction of cytosolic phospholipase $A_2$ by oncogenic Ras in human non-small cell lung cancer. *J. Biol. Chem.* 272:14501-14504; 1997.

Gupta, S.; Srivastava, M.; Ahmad, N.; Sakamoto, K.; Bostwick, D. G.; Mukhtar, H. Lipoxygenase-5 is overexpressed in prostate adenocarcinoma. *Cancer* 91:737-743; 2001.

Hennig, R.; Ding, X. Z.; Tong, W. G.; Schneider, M. B.; Standop, J.; Friess, H.; Buchler, M. W.; Pour, P. M.; Adrian, T. E. 5-Lipoxygenase and leukotriene B(4) receptor are expressed in human pancreatic cancers but not in pancreatic ducts in normal tissue. *Am. J. Pathol.* 161:421-428; 2002.

Jiang, W. G; Douglas-Jones, A.; Mansel, R. E. Levels of expression of lipoxygenases and cyclooxygenase-2 in human breast cancer. *Prostaglandins Leuko. Essent. Fatty Acids* 69:275-281; 2003.

Matsuyama, M.; Yoshimura, R.; Mitsuhashi, M.; Hase, T.; Tsuchida, K.; Tkemoto, Y.; Kawahito, Y.; Sano, H.; Nakatani, T. Expression of lipoxygenase in human prostate cancer and growth reduction by its inhibitors. *Int. J. Oncol.* 24:821-827; 2004.

Ding, X. Z.; Talamonti, M. S.; Bell, R. H.; Adrian, T. E. A novel anti-pancreatic cancer agent, LY293111. *Anticancer Drugs* 16:467-473; 2005.

Tong, W. G.; Ding, X. Z.; Hennig, R.; Witt, R. C.; Standop, J.; Pour, P. M.; Adrian, T. E. Leukotriene $B_4$ receptor antagonist LY293111 inhibits proliferation and induces apoptosis in human pancreatic cancer cells. *Clin. Cancer Res.* 8:3232-3242; 2002.

The invention claimed is:

1. A method for treating a patient with cancer, which comprises administering a therapeutically effective amount of an antisense oligonucleotide that inhibits the expression or intracellular signaling of leukotriene B4 receptor-2 (BLT2) to the patient, wherein the antisense oligonucleotide consists of the sequence of SEQ ID NO: 6.

2. The method according to claim 1, wherein the cancer is a human cancer.

3. The method according to claim 1, wherein the antisense oligonucleotide inhibits the upstream or downstream signaling pathway of BLT2.

4. The method according to claim 2, wherein the human cancer is a cancer that over-expresses BLT2 protein or oncogenic Ras.

5. The method according to claim 4, wherein the human cancer is selected from the group consisting of bladder, prostate, pancreatic, and breast cancer.

6. The method according to claim 2, wherein the treatment of human cancer is accomplished by inducing the apoptosis of cancer cells, inhibiting the metastasis of cancer cells, or inhibiting the angiogenesis of tumor.

7. The method according to claim 2, further comprising administering an anti-cancer drug for the treatment of human cancer.

8. A method for treating a patient with cancer, which comprises administering a therapeutically effective amount of an siRNA that inhibits the expression or intracellular signaling of leukotriene B4 receptor-2 (BLT2) to the patient, wherein the siRNA has a sense sequence of SEQ ID NO: 7 and an antisense sequence of SEQ ID NO: 8.

9. The method according to claim 8, wherein the cancer is a human cancer.

10. The method according to claim 8, wherein the siRNA inhibits the upstream or downstream signaling pathway of BLT2.

11. The method according to claim 9, wherein the human cancer is a cancer that over-expresses BLT2 protein or oncogenic Ras.

12. The method according to claim 11, wherein the human cancer is selected from the group consisting of bladder, prostate, pancreatic, and breast cancer.

13. The method according to claim 9, wherein the treatment of human cancer is accomplished by inducing the apoptosis of cancer cells, inhibiting the metastasis of cancer cells, or inhibiting the angiogenesis of tumor.

14. The method according to claim 9, further comprising administering an anti-cancer drug for the treatment of human cancer.

* * * * *